(12) United States Patent
Schraga

(10) Patent No.: US 8,303,614 B2
(45) Date of Patent: Nov. 6, 2012

(54) DOUBLE-ENDED LANCET, METHOD AND LANCET DEVICE USING THE DOUBLE-ENDED LANCET, AND METHOD OF ASSEMBLING AND/OR MAKING THE DOUBLE-ENDED LANCET

(75) Inventor: Steve Schraga, North Miami, FL (US)

(73) Assignee: Stat Medical Devices, Inc., North Miami, FL (US)

( * ) Notice: Subject to any disclaimer, the term of this patent is extended or adjusted under 35 U.S.C. 154(b) by 1831 days.

(21) Appl. No.: 11/312,433

(22) Filed: Dec. 21, 2005

(65) Prior Publication Data

US 2007/0142854 A1    Jun. 21, 2007

(51) Int. Cl.
*A61B 17/32* (2006.01)
(52) U.S. Cl. ........................................ 606/181
(58) Field of Classification Search ............... 606/181, 606/182, 183; 600/583, 584
See application file for complete search history.

(56) References Cited

U.S. PATENT DOCUMENTS

| | | | | |
|---|---|---|---|---|
| 2,539,510 A * | 1/1951 | Friden | ............ | 604/192 |
| 3,294,089 A * | 12/1966 | Brookfield | ............ | 604/241 |
| 3,517,670 A * | 6/1970 | Speelman | ............ | 606/181 |
| 3,968,876 A * | 7/1976 | Brookfield | ............ | 206/365 |
| 5,328,466 A * | 7/1994 | Demark | ............ | 604/189 |
| 5,395,388 A | 3/1995 | Schraga | | |
| 5,454,828 A | 10/1995 | Schraga | | |
| 5,613,978 A | 3/1997 | Harding | | |
| 5,643,306 A | 7/1997 | Schraga | | |
| 5,941,857 A * | 8/1999 | Nguyen et al. | ............ | 604/263 |
| 6,589,261 B1 | 7/2003 | Abulhaj et al. | | |
| 2002/0151849 A1 * | 10/2002 | West et al. | ............ | 604/181 |
| 2002/0169470 A1 | 11/2002 | Kuhr et al. | | |
| 2003/0050573 A1 | 3/2003 | Kuhr et al. | | |
| 2004/0260325 A1 | 12/2004 | Kuhr et al. | | |
| 2005/0021066 A1 | 1/2005 | Kuhr et al. | | |
| 2006/0174592 A1 * | 8/2006 | Chan | ............ | 53/442 |

OTHER PUBLICATIONS

U.S. Appl. No. 11/138,277 in the name of Schraga, filed May 27, 2005.
U.S. Appl. No. 10/988,636 in the name of Schraga, filed Nov. 16, 2004.
U.S. Appl. No. 11/035,978 in the name of Schraga, filed Jan. 18, 2005.
U.S. Appl. No. 11/073,736 in the name of Schraga, filed Dec. 2, 2004.

* cited by examiner

*Primary Examiner* — Tuan V Nguyen
(74) *Attorney, Agent, or Firm* — Greenblum & Bernstein, P.L.C.

(57) ABSTRACT

Double-ended lancet unit for a lancet device. The unit includes a lancet body having a first end and a second end and being sized and configured to frictionally engage with a holding member of the lancet device. A first lancet needle projects from the first end and a second lancet needle projects from the second end and/or a lancet needle member has oppositely arranged pointed ends and is movably mounted to the lancet body. The body is made of a material different from that of the first and second needles or the pointed ends. First and second removable caps are respectively removably connected to the first and second ends. At least one of the first and second removable caps are re-installable on one of the first and second ends of the double-ended lancet unit. The unit is installable on the lancet device and each of the first and second needles or the pointed ends is structured and arranged to prick a user's skin to obtain a blood sample and is not usable for fluid injection.

35 Claims, 25 Drawing Sheets

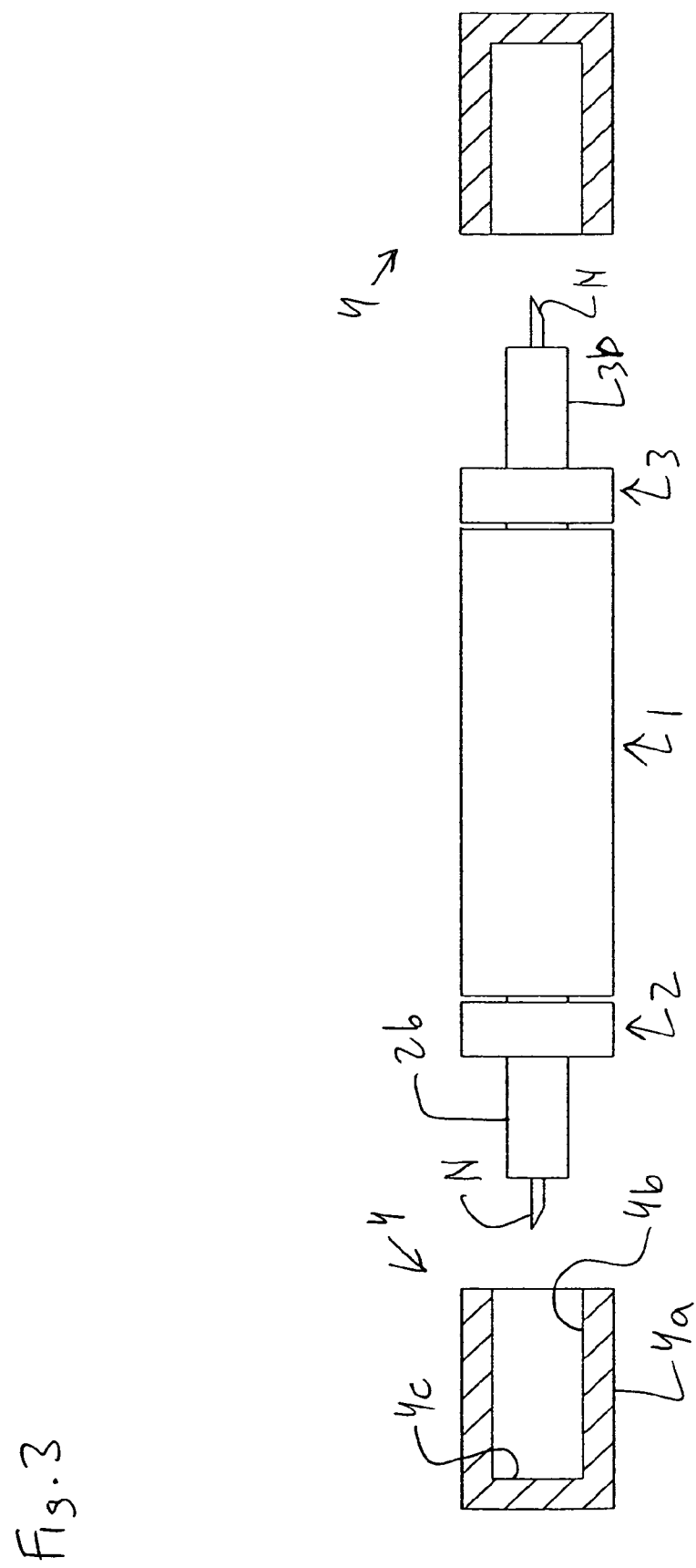

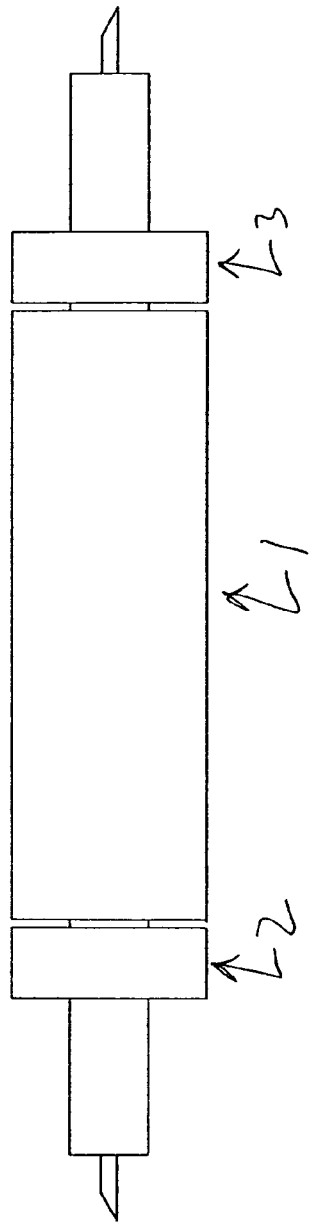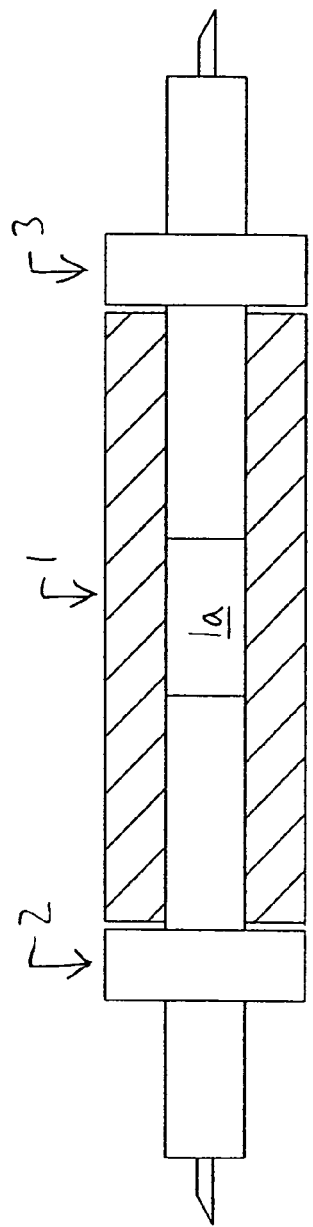

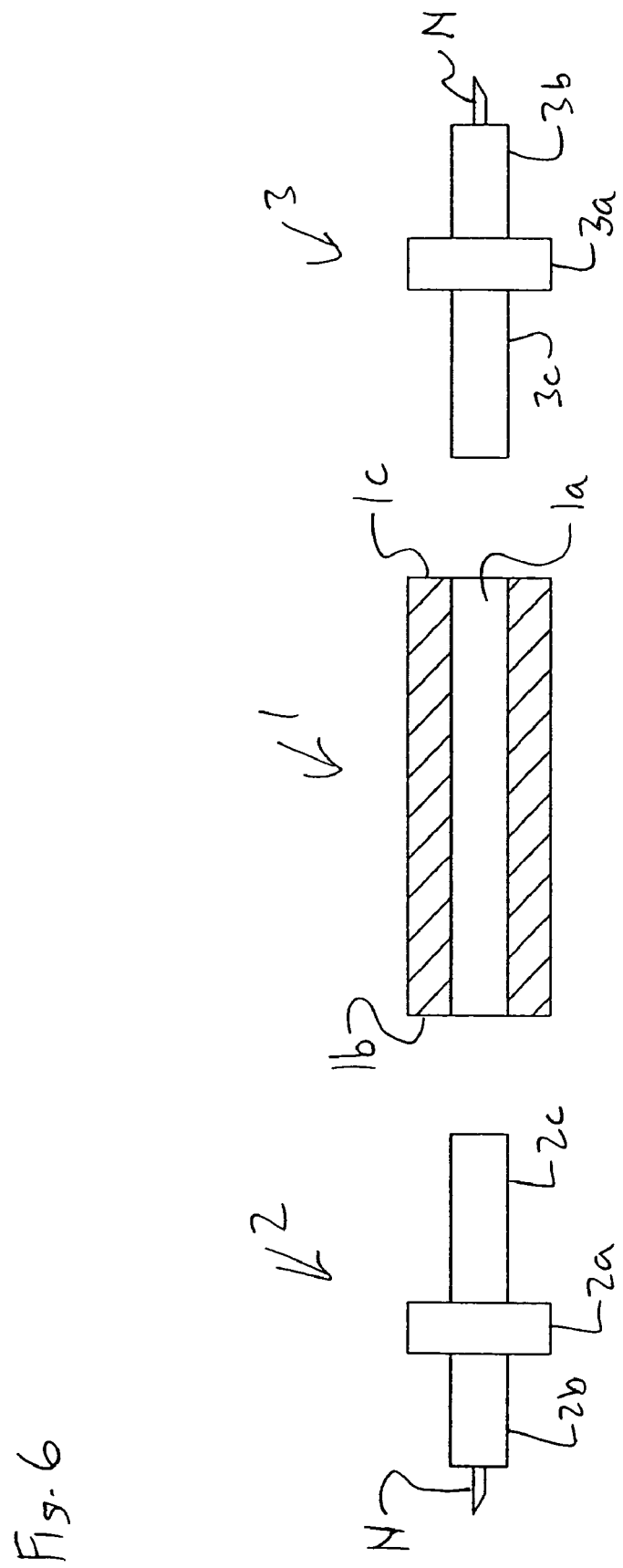

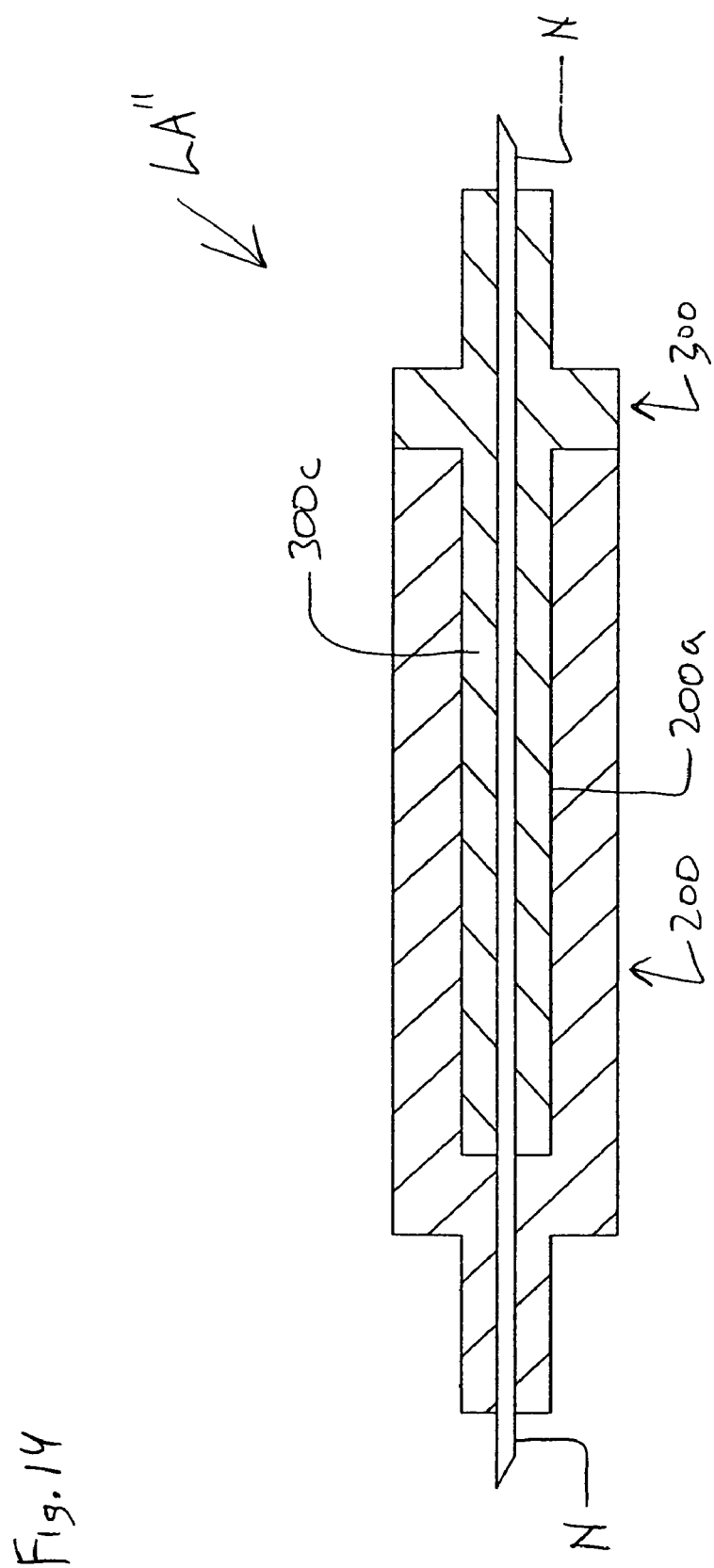

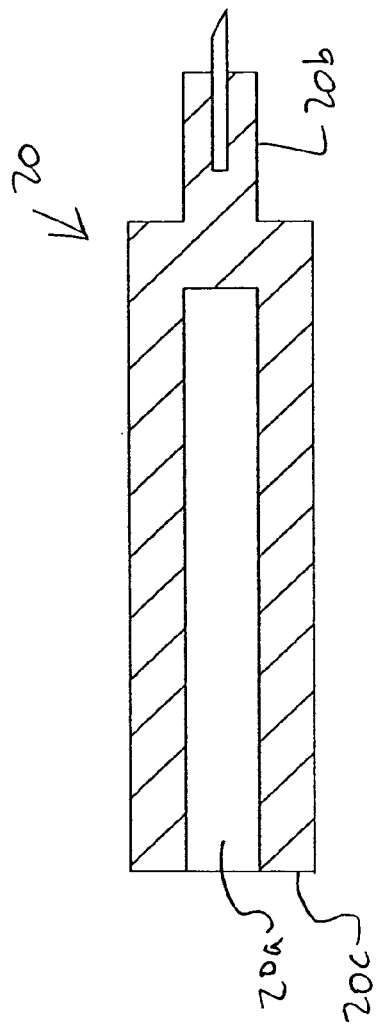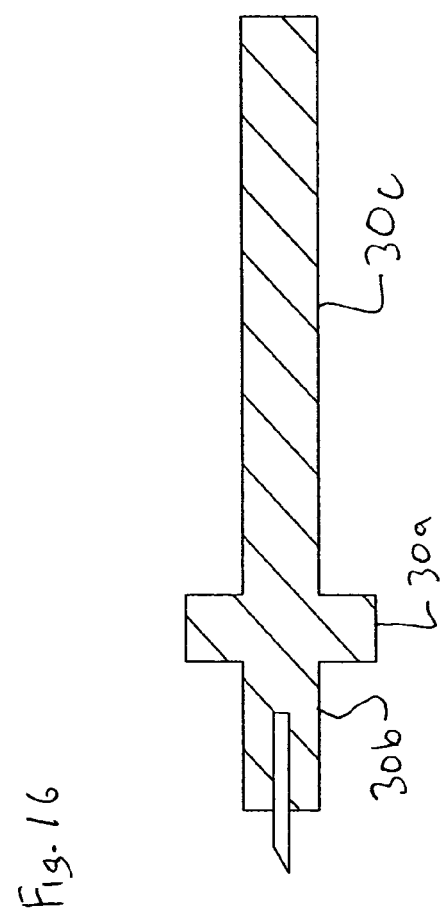

FC    LB    SC    LA^IV

SC

SC

SC    FC

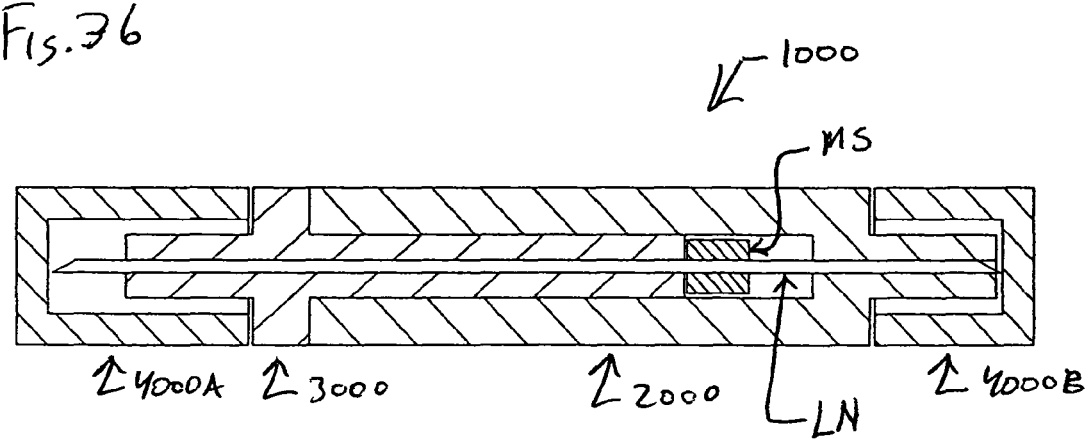
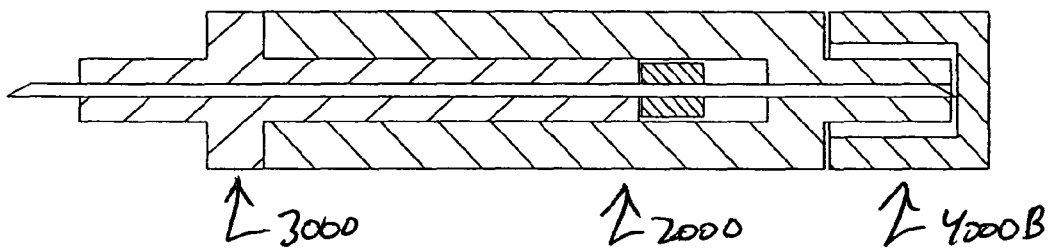
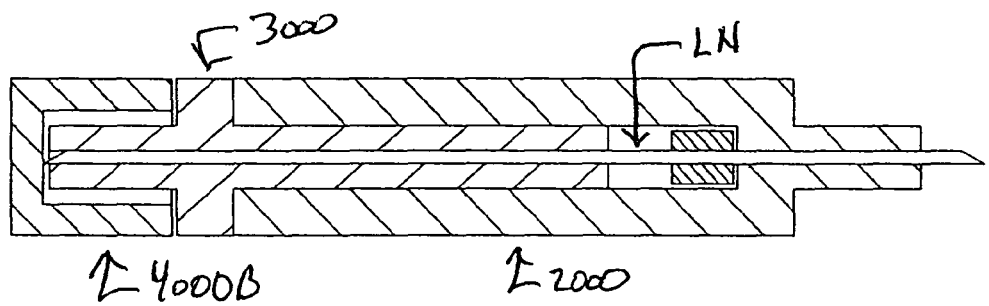
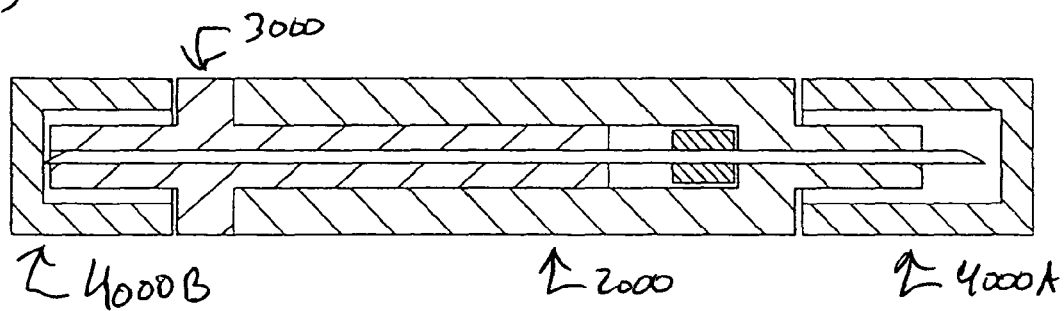

DOUBLE-ENDED LANCET, METHOD AND LANCET DEVICE USING THE DOUBLE-ENDED LANCET, AND METHOD OF ASSEMBLING AND/OR MAKING THE DOUBLE-ENDED LANCET

BACKGROUND OF THE INVENTION

1. Field of the Invention

The invention relates to a double-ended lancet in which two opposite facing lancet needles are arranged on a lancet. The lancet needles can be removably connected to each other and can be disconnected from each other by twisting, pulling, bending, and/or any combination of these movements. The lancet can also have two protective caps, each cap covering one of the lancet needles. The invention also relates to a method of assembling and/or forming the double-ended lancet assembly by individually forming each lancet part, and connecting the lancet parts together in order to form a double-ended lancet unit. The invention further relates to a lancet device which uses the double-ended lancet unit and to a method of using the lancet device to puncture a user's skin. The invention also relates to a method which involves replacing the lancet typically used with a lancet device with the lancet unit of the invention so that the lancet can be used twice as much, in comparison with conventional lancets, prior to being discarded.

2. Discussion of Background Information

Lancet devices are commonly used to prick the skin of the user so that one or more drops of blood may be extracted for testing. Some users, such as diabetics, for example, may have to test their blood sugar levels several times a day. This may be accomplished by the user using a simple needle. However, this procedure is often problematic for the user since the needle may be difficult to handle. Additionally, many users simply cannot perform the procedure owing to either a fear of needles or because they lack a steady hand. As a result, lancet devices have been developed which allow the user to more easily and reliably perform this procedure. Prior art lancets typically have one usable end which when used up means that the lancet is ready to be discarded. Because lancets are used often enough, it would be beneficial and economical to maximize the use of lancets prior to them being discarded.

SUMMARY OF THE INVENTION

According to one illustrative aspect of the invention there is provided a double-ended lancet unit for a lancet device which can double the useful life of the lancet compared with a conventional lancet. The unit comprises a lancet body having a first end and a second end. The unit can include at least one of a first lancet needle projects from the first end and a second lancet needle projects from the second end and a lancet needle member having oppositely arranged pointed ends and being movably mounted to the lancet body.

The lancet body may comprise a one-piece integrally formed member. The lancet body may comprise a one-piece synthetic resin member. The lancet body may comprise a two-piece member with non-removably connected portions. The lancet body may comprise a two-piece member with removably connected portions. The first and second lancet needles may be made of metal and project from the first and second ends by substantially a same amount. The lancet unit may have an overall length which between approximately 0.25 inches and approximately 1.50 inches. The lancet body may be generally cylindrical. The lancet body may comprise a diameter that is between approximately 0.125 inches and approximately 0.375 inches. Each of the plurality of lancets may comprise a generally cylindrical portion.

The unit may further comprise first and second caps respectively removably connected to the first and second ends. The unit may alternatively further comprise first and second caps respectively non-removably connected to the first and second ends.

The unit may further comprise a first cap removably connected to the first end, and once installed on the second end, non-removably connected to the second end. The unit may further comprise a second cap removably connected to the second end, and being capable of being installed on the first end. The unit may further comprise a second cap removably connected to the second end, and once installed on the first end, non-removably connected to the first end.

The lancet body may comprise a main portion and first and second portions connected to the main portion. The lancet body may have an outer member and an inner member extending at least partially into the outer member. The lancet body may comprise one of a polygonal cross-section, an oval cross-section, a non-circular cross-section, and a circular cross-section.

The unit may further comprise first and second caps respectively connected to the first and second ends via respective first and second locking mechanisms. The unit may further comprise first and second caps respectively connected to the first and second ends via respective first and second breakable connection mechanisms.

The invention also provides for a lancet device utilizing the double-ended lancet unit of the type described above, wherein the lancet device comprises a body and a holding member which removably retains the double-ended lancet unit.

The invention also provides for a lancet device utilizing the double-ended lancet unit of the type described above, wherein the lancet device comprises a body, a trigger and a movable holding member which removable retains the double-ended lancet unit.

The invention also provides for a lancet device utilizing the double-ended lancet unit of the type described herein, wherein the lancet device comprises a body, a trigger, a movable holding member which retains the double-ended lancet unit, and a mechanism for moving the holding member to a retracted trigger-set position.

The invention also provides for a lancet device utilizing the double-ended lancet unit of the type described above, wherein the lancet device comprises a body, a holding member which retains the double-ended lancet unit, and a cap removably connected to the body.

The invention also provides for a method of puncturing a surface of skin using the lancet device of the type described above, wherein the method comprises arranging the lancet device adjacent against a user's skin and triggering the lancet device so that one of the first and second lancet needles is caused to penetrate the user's skin.

The invention also provides for a method of puncturing a surface of skin using the lancet device of the type described above, wherein the method comprises arranging the cap adjacent against a user's skin, triggering the lancet device so that the first lancet needle is caused to penetrate the user's skin, removing the lancet unit from the holding member and re-installing the lancet unit onto the holding member, and again triggering the lancet device so that the second lancet needle is caused to penetrate the user's skin.

The method may further comprise disconnecting, before the removing, a first cap from the first end and installing the first cap on the second end.

The invention also provides for a method of puncturing a surface of skin using the lancet device of the type described above, wherein the method comprises installing the lancet unit onto the holding member, disconnecting a first cap from the first end, arranging the lancet device adjacent against a user's skin, triggering the lancet device so that the first lancet needle is caused to penetrate the user's skin, removing the lancet unit from the holding member, disconnecting a second cap from the second end and installing the second cap on the first end, re-installing the lancet unit onto the holding member, and again triggering the lancet device so that the second lancet needle is caused to penetrate the user's skin.

The invention also provides for a double-ended lancet unit for a lancet device, wherein the unit comprises a body having first and second generally symmetrical ends, a first needle projecting from a center of a generally planar surface arranged on the first end, a second needle projecting from a center of a generally planar surface arranged on the second end, a first cap removably connected to the first end, and a second cap removably connected to the second end.

The body may comprises a color X such as, e.g., blue. The first cap may comprise a color substantially similar to color X such as, e.g., blue or light blue. The second cap may comprise a color that is substantially different from color X such as, e.g., red.

The body and the first cap have substantially the same color and the second cap comprises a different color than the body.

The invention also provides for a double-ended lancet unit for a lancet device, wherein the unit comprises a body having first and second generally symmetrical ends, a first needle projecting from a center of a generally planar surface arranged on the first end, a second needle projecting from a center of a generally planar surface arranged on the second end, a first cap connected to the first end via one of a breakable connection and a locking connection, and a second cap connected to the second end via one of a breakable connection and a locking connection.

The body and the first cap may have substantially the same color and the second cap may comprise a different color than the first cap and the body. Once removed from the first end and installed on the second end, the first cap may remain non-removably connected to the second end.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 3 shows another side view of the embodiment shown in FIG. 1 with the end caps disconnected and/or removed from the ends of the lancet body;

FIG. 4 shows another side view of the embodiment shown in FIG. 1 with the end caps removed;

FIG. 5 shows a side view of FIG. 4 with the main body portion shown in cross-section;

FIG. 6 shows a side view of FIG. 5 with end portions disconnected from the main portion;

FIG. 14 shows, in cross-section, an alternative embodiment of the lancet body with the caps removed;

FIG. 15 shows a cross-section view of the outer portion used in the embodiment of FIGS. 11-13;

FIG. 16 shows a cross-section view of the inner portion used in the embodiment of FIGS. 11-13;

FIG. 36 shows still another embodiment of the lancet unit of the invention. This embodiment is similar to that of FIG. 14 except that it uses different size left and right cap. As a result of this arrangement, the right side cap can be removed from the right end and installed onto the left end of the lancet body and vice versa thereby causing axial movement of the lancet needle member. In the position shown in FIG. 36, the right side cap moves the right side pointed end of the needle so as to be substantially flush with the right axial end face of the outer part of the body. The right side cap also prevents the lancet needle from moving axially to the right;

FIG. 37 shows the embodiment of FIG. 36 with the left side cap removed from the left end;

FIG. 38 shows the embodiment of FIG. 36 with the right side cap removed from the right end and installed on the left end. Installation of the right cap on the left end causes the lancet needle to move axially to the right;

FIG. 39 shows the embodiment of FIG. 36 with the right side cap installed on the left end and with the left side cap installed on the right end.

DETAILED DESCRIPTION OF THE PRESENT INVENTION

Figure 1:
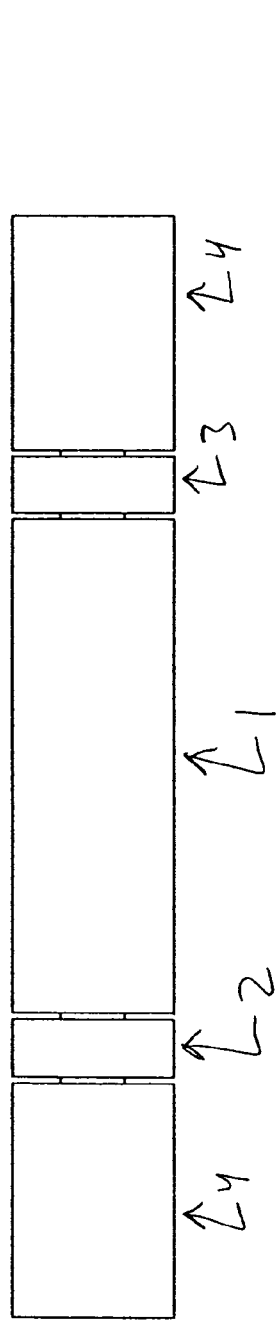
FIG. 1 shows a side view of one embodiment of a double-ended lancet unit. The unit includes two removably connected caps and a lancet body made up of three portions; a main portion and two end portions connected to opposite ends of the main portion.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

FIGS. 1-10 show a first non-limiting embodiment of a lancet assembly or double-ended lancet unit LA. The unit LA includes a main body portion 1, a first end portion 2 and a second end portion 3. The first and second end portions 2, 3 are oriented in opposite directions. Each end portion 2, 3 also includes a cap 4 to protect a lancet needle, as will be described later on. The main body 1 can have any desired cross-sectional shape such as polygonal, circular, or oval, and preferably is either triangular, square or circular in order to fit snugly into existing holding members of existing lancet devices. In the embodiment shown in FIGS. 1-10, the main body 1 has a generally cylindrical shape having a length of between approximately 0.25 inches and approximately 1 inch and a diameter of between approximately 0.05 inches and approximately 0.3 inches. The particular size and shape of the lancet unit LA can, of course, be adapted to the particular size and shape requirements of the lancet device. The first and second end portions 2 and 3 have portions which frictionally engage with an inside opening 1a. Preferably, the opening 1a is sized and shaped so that the end portions 2 and 3 can be prevented from being removed once they are positioned therein. This connection can be effectuated by any desired connection such as a press-fit connection, an adhesive connection, or an ultrasonic welding connection, etc,.

The caps 4 can have any desired shape and are preferably removably connected to the first and second end portions 2, 3 (or the main body 1). In the embodiment shown in FIGS. 1-10, the caps 4 can be generally cylindrical in shape. By way of non-limiting example, the caps 4 can have a diameter which substantially corresponds to that of the main body and a length which is between about 0.1 inches long and about 0.3 inches long. The caps 4 are also preferably made of synthetic resin (and preferably of the same material used for conventionally known lancets) and of the same material as the main body 1 and end portions 2, 3. Most preferably, the left side cap 4 is made to have a color that corresponds to the color of the first end portion 2 and the right side cap 4 is made to have a color that corresponds to the color of the second end portion 3 with the colors of the end portions 2 and 3 being different. For example, the left side cap 4 can be made to have a blue color that corresponds to a blue color of the first end portion 2 and the right side cap 4 can be made to have a red color that corresponds to the red color of the second end portion 3.

The benefits of such an arrangement is as follows: a user installs the lancet unit LA onto a holding member of the lancet device (in a similar manner to that shown in FIG. 29) with, e.g., the red end 3 projecting out from the holding member. Then, he or she removes the red cap 4 and uses the lancet device to prick the skin. Then, instead of discarding the lancet unit LA (as is the case with the prior art lancets), he or she removes the lancet unit LA from the holding member and removes the blue cap 4 from the blue end 2, installs the blue cap 4 on the red end 3. Then, he or she re-installs the lancet unit LA into the holding member with the blue end 2 projecting from the holding member. The user is now free to prick the skin with another clean needle. After use, the user will know that the lancet unit LA is used up because, once removed from the holding member, the user will see that red cap 4 is installed on the blue end 2-indicating that that needle has been used already. He or she can then install the blue cap 4 on the red end 3 and discard the lancet unit LA. This process doubles the useful file of the lancet.

Figure 2:
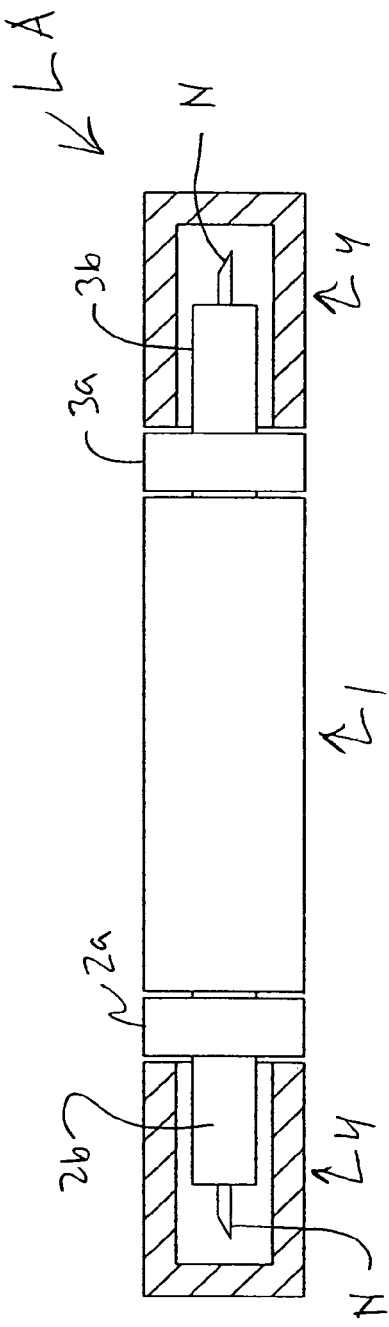
FIG. 2 shows another side view of the embodiment of FIG. 1 with the end caps shown in cross-section.
Figure 17:
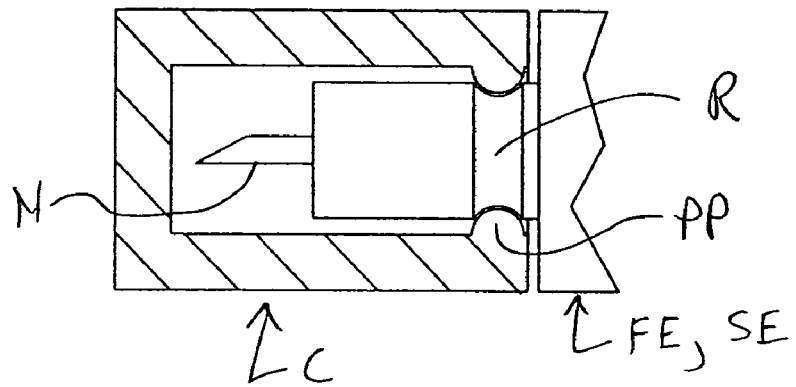
FIG. 17 shows a partial side view of one way that the caps of any of the embodiments disclosed herein can be secured to the lancet body. In this embodiment, the caps are of a one-piece construction and are each connected via a projection and recess connection.
Figure 18:
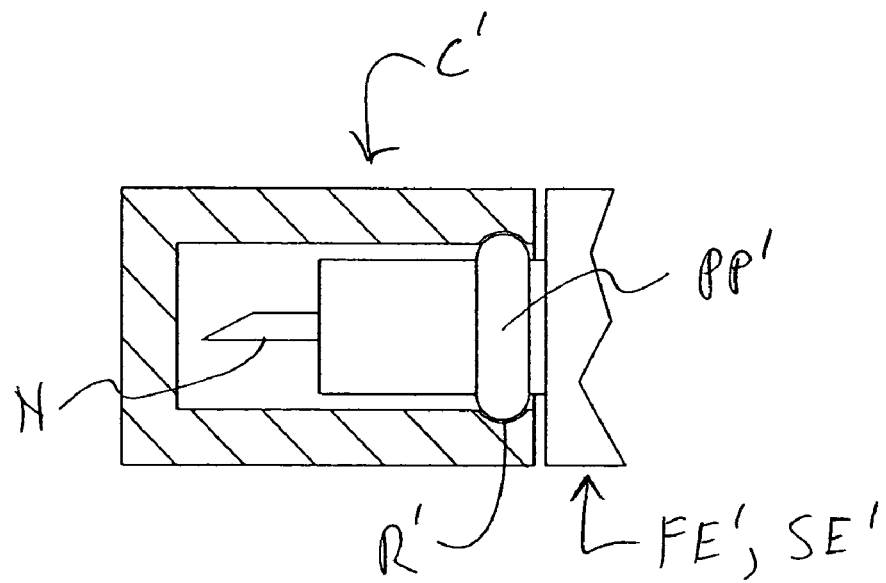
FIG. 18 shows a partial side view of another way that the caps of any of the embodiments disclosed herein can be secured to the lancet body. In this embodiment, the caps are of a one-piece construction and are each connected via a recess and projection connection.
Figure 19:
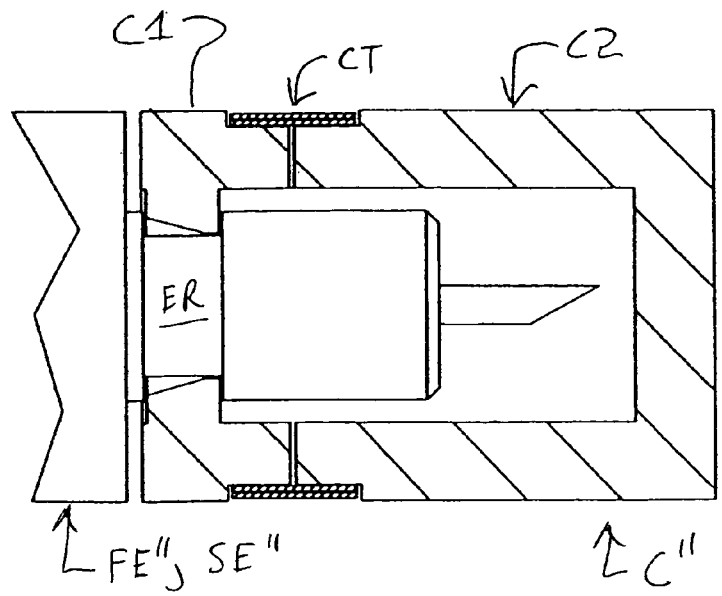
FIG. 19 shows a partial side view of still another way that the caps of any of the embodiments disclosed herein can be secured to the lancet body. In this embodiment, the cap is shown in cross-section and is of a two-piece construction which pieces are connected together via a breakable tape which is wrapped about the connection between both pieces.
Figure 20:
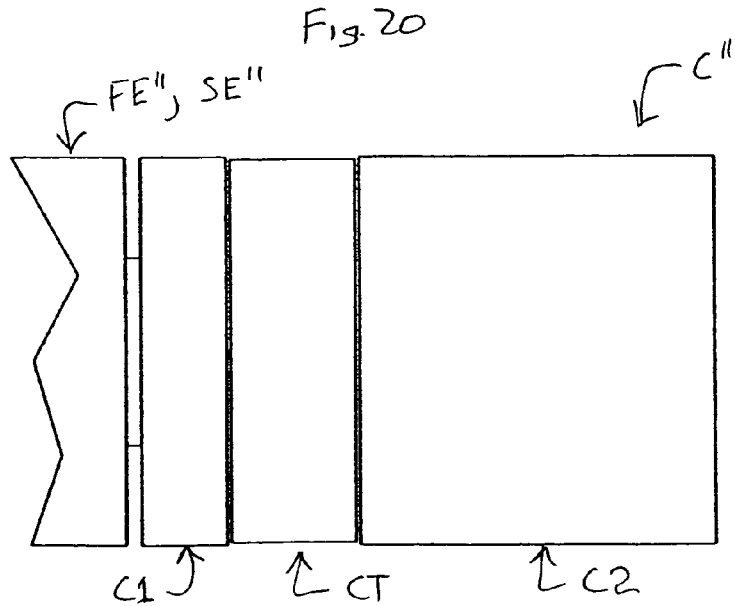
FIG. 20 shows a side non-cross-section view of FIG. 19.
Figure 22:
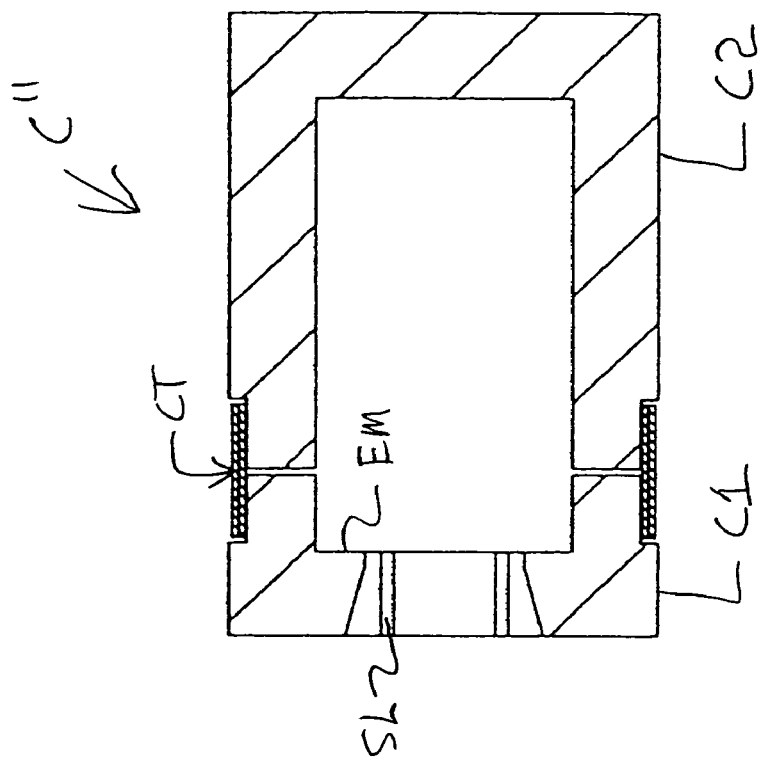
FIG. 22 shows a side cross-section view of the cap used in FIGS. 19 and 20 prior to the cap being installed onto the end portion shown in FIG. 21.
Figure 21:
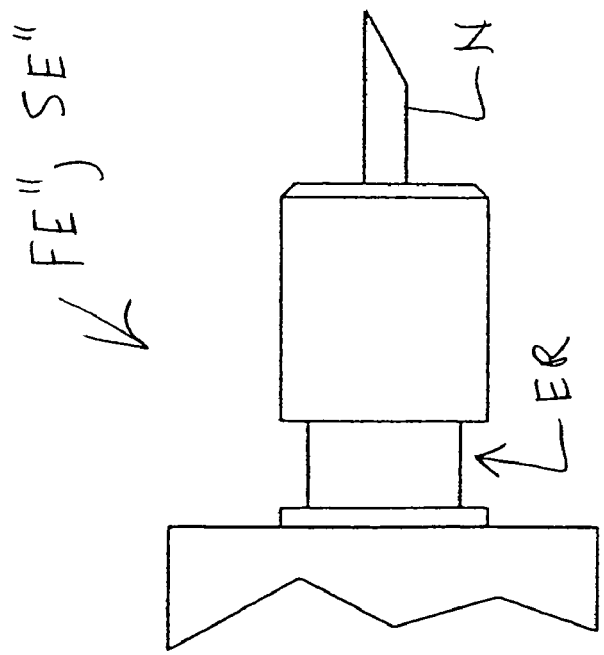
FIG. 21 shows a side non-cross-section view of FIGS. 19 and 20 with the cap removed.
Figure 24:
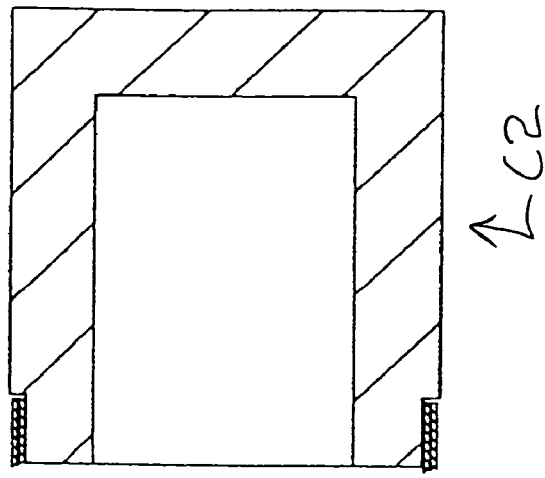
FIG. 24 shows a side view of FIG. 22 after the outer end portion of the cap is separated along the breakable connection formed by the wrapped tape.
Figure 23:
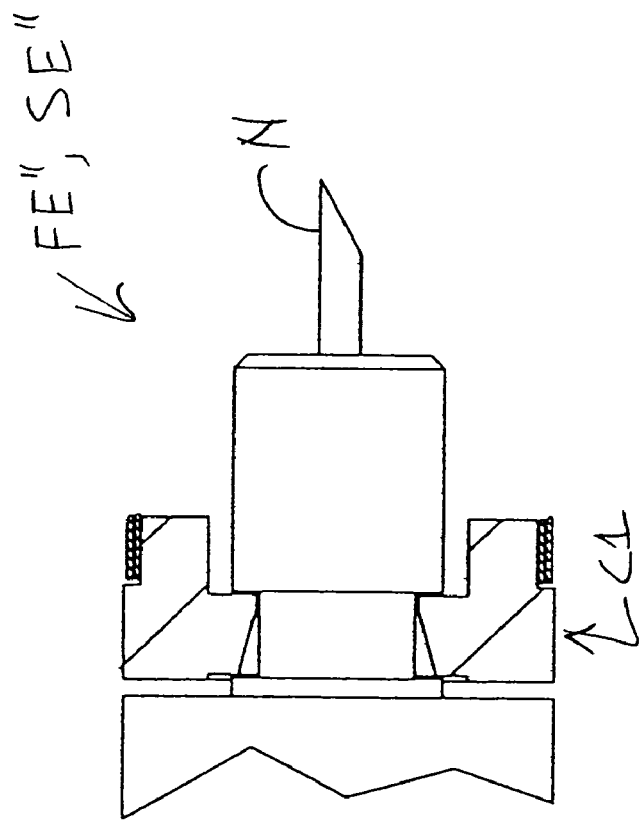
FIG. 23 shows a side view of FIG. 19 after the outer end portion of the cap is separated along the breakable connection formed by the wrapped tape.

As can be seen in FIGS. 2 and 3, the caps 4 have an inner surface 4b which can be cylindrical which slides over and onto the projecting portions 2b, 3b of the end portions 2, 3. Although not shown in FIGS. 1-10, the invention contemplates some sort of mechanical connection between the caps 4 and the end portions 2, 3. In this regard, various non-limiting connection arrangements are shown in the drawings which can be used in this embodiment. Preferably, for the embodiment shown in FIGS. 1-10, a connection arrangement of the type shown in FIGS. 17 and 18 is used in this embodiment. Most preferably, a connection system similar to that of FIGS. 32-35 is used in the embodiment of FIG. 1-10. Each cap 4 also has a closed end 4c which is preferably spaced from the end of the needle N in order to prevent injury to the needle N.

Figure 8:
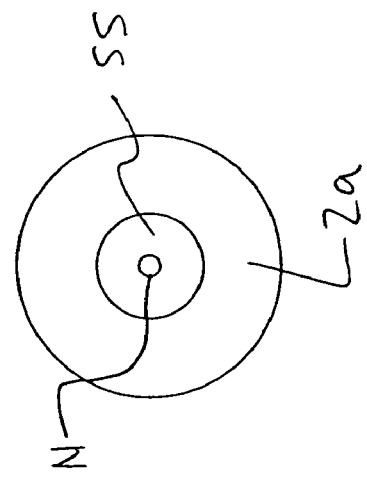
FIG. 8 shows an end view of FIG. 7.
Figure 7:
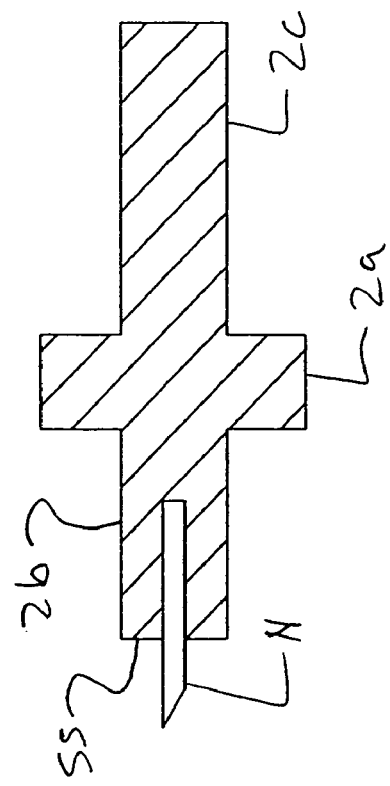
FIG. 7 shows a cross-section view of the left end portion shown in FIG. 6.
Figure 10:
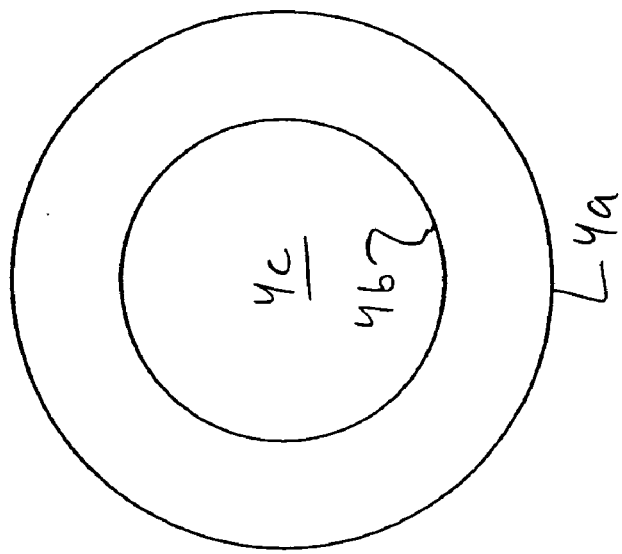
FIG. 10 shows an end view of the cap shown in FIG. 9.
Figure 9:
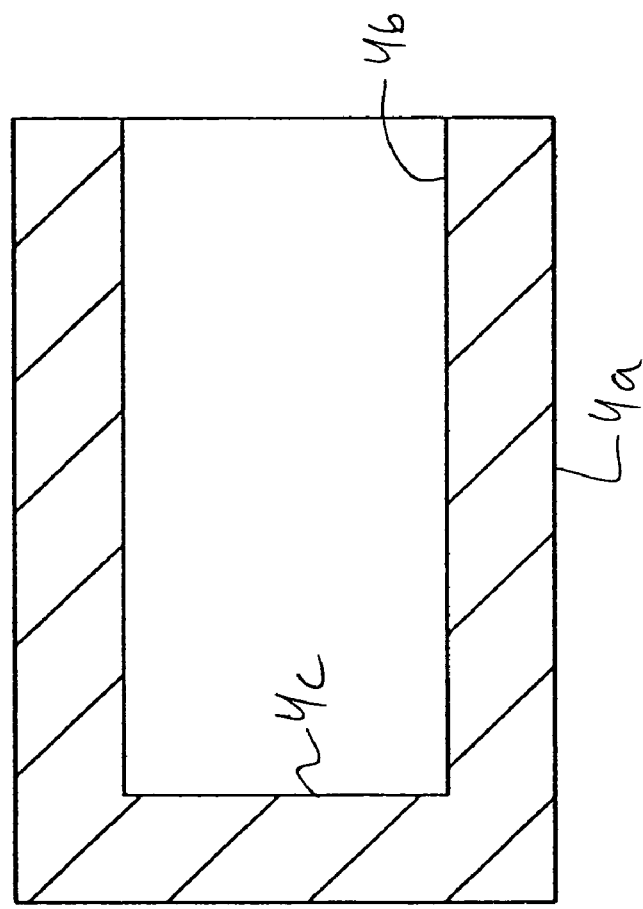
FIG. 9 shows a cross-section view of the protective cap used in the embodiment shown in FIG. 1.

The end portions 2, 3 have a shoulder or flange portion 2a, 3a, which can be of any size and shape and preferably correspond to that of the main body 1. The flange portion 2a of the first end portion 2 is preferably arranged to abut (or to be slightly spaced therefrom) the first end 1b of the main body 1 and the flange portion 3a of the second end portion 3 is preferably arranged to abut (or to be slightly spaced therefrom) the second end 1c of the main body 1. As can be seen in FIGS. 6-8, the first end portion 2 and the second end portion 3 are generally identical in configuration. Each portion 2, 3 includes a flange portion 2a, 3a (as described above) as well as a front portion 2b, 3b which supports the needle N and whose front surface SS contacts the cap of the lancet device in order to define the penetration depth (see e.g., FIG. 31). Each portion 2, 3 further includes a rear portion 2c, 3c which is sized and shaped to connect with the inner opening 1a of the main body 1. The length of generally cylindrical portion 2c and 3c can be any desired length and is preferably between 0.03 inches and 0.2 inches. Each portion 2 and 3 is preferably made as a one piece synthetic resin member that is formed with a metal needle N installed therein, e.g., in the same way that conventional lancets are formed. Preferably, the needle N projects from the stop surface SS by an amount that is typical of conventional lancets.

FIGS. 11-13, 15 and 16 show a second non-limiting embodiment of a lancet assembly or double-ended lancet unit LA'. Unlike the previous embodiment using three-piece body, the unit LA' of this embodiment does not utilize a main body portion, and instead utilizes only a first end portion 20 and a second end portion 30. The first and second end portions 20, 30 are oriented in opposite directions. Each end portion 20, 30 also includes a cap 40 to protect a lancet needle, as will be described later on. The first portion 20 can have any desired cross-sectional shape such as polygonal, circular, or oval, and preferably is either triangular, square or circular in order to fit snugly into existing holding members of existing lancet devices. In the embodiment shown in FIGS. 11-13, 15 and 16, the outer portion 20 has a generally cylindrical shape having a length of between approximately 0.25 inches and approximately 1 inch and a diameter of between approximately 0.05 inches and approximately 0.3 inches. The particular size and shape of the lancet unit LA' can, of course, be adapted to the particular size and shape requirements of the lancet device as is the case with the previous embodiment. The first end portion 20 has an inner opening 20a which frictionally engages with an outer surface 30c. Preferably, the opening 20a and the correspondingly shaped cylindrical portion 30c are sized and shaped so that the end portions 20 and 30 can be prevented from being removed or disconnected from each other once they are connected. This connection can be effectuated by any desired connection such as a press-fit connection, an adhesive connection, or an ultrasonic welding connection, etc,.

The caps 40 can have any desired shape and are preferably removably connected to the first and second end portions 20, 30. In the embodiment shown in FIGS. 11-13, 15 and 16, the caps 40 can be generally cylindrical in shape. By way of non-limiting example, the caps 40 can have a diameter which substantially corresponds to that of the portions 20, 30 and a length which is between about 0.1 inches long and about 0.3 inches long. The caps 40 are also preferably made of synthetic resin (and preferably of the same material used for conventionally known lancets) and of the same material as the end portions 20, 30. Most preferably, the left side cap 40 is made to have a color that corresponds to the color of the first end portion 20 and the right side cap 40 is made to have a color that corresponds to the color of the second end portion 30 with the colors of the end portions 20 and 30 being different. For example, the left side cap 40 can be made to have a blue color that corresponds to a blue color of the first end portion 20 and the right side cap 40 can be made to have a red color that corresponds to the red color of the second end portion 30.

The benefits of such an arrangement is as follows: a user installs the lancet unit LA' onto a holding member of the lancet device (in a similar manner to that shown in FIG. 29) with, e.g., the red end 30 projecting out from the holding member. Then, he or she removes the red cap 40 and uses the lancet device to prick the skin. Then, instead of discarding the lancet unit LA' (as is the case with the prior art lancets), he or she removes the lancet unit LA' from the holding member and removes the blue cap 40 from the blue end 20, installs the blue cap 40 on the red end 30. Then, he or she re-installs the lancet unit LA' into the holding member with the blue end 20 projecting from the holding member. The user is now free to prick the skin with another clean needle. After use, the user will know that the lancet unit LA' is used up because, once removed from the holding member, the user will see that red cap 40 is installed on the blue end 20—indicating that that needle has been used already. He or she can then install the blue cap 40 on the red end 30 and discard the lancet unit LA'. This process doubles the useful file of the lancet.

Figure 11:
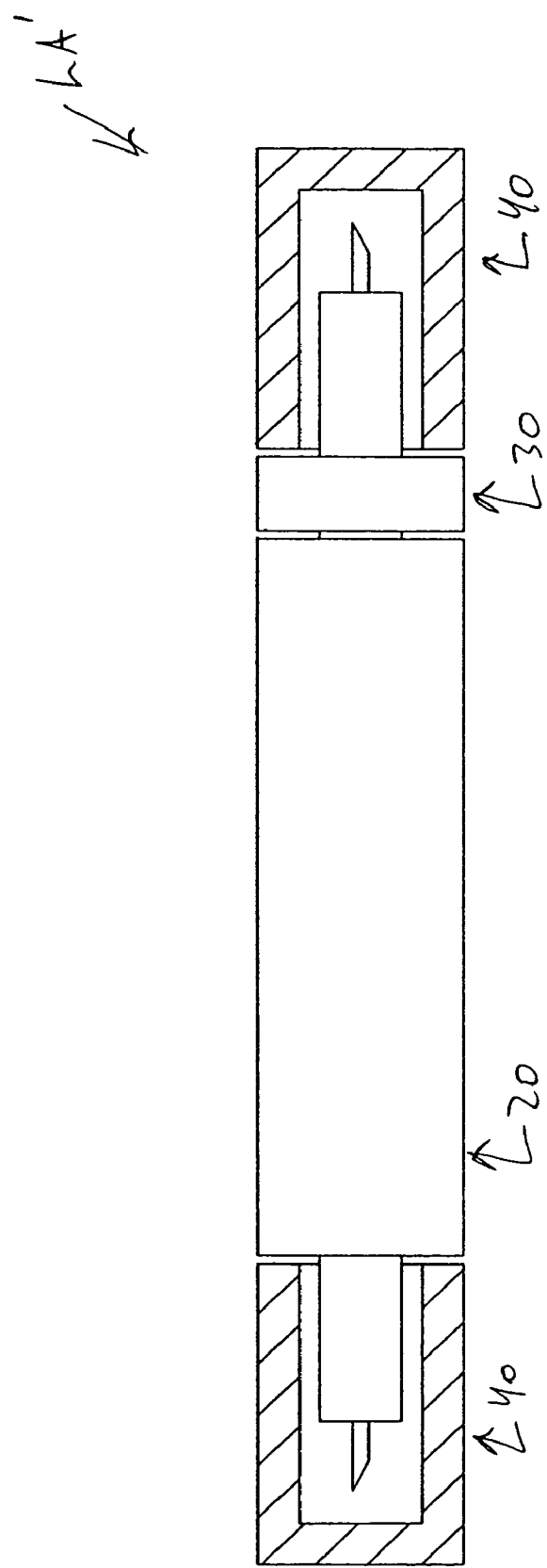
FIG. 11 shows another embodiment of the invention. The protective caps are shown in cross-section.
Figure 12:
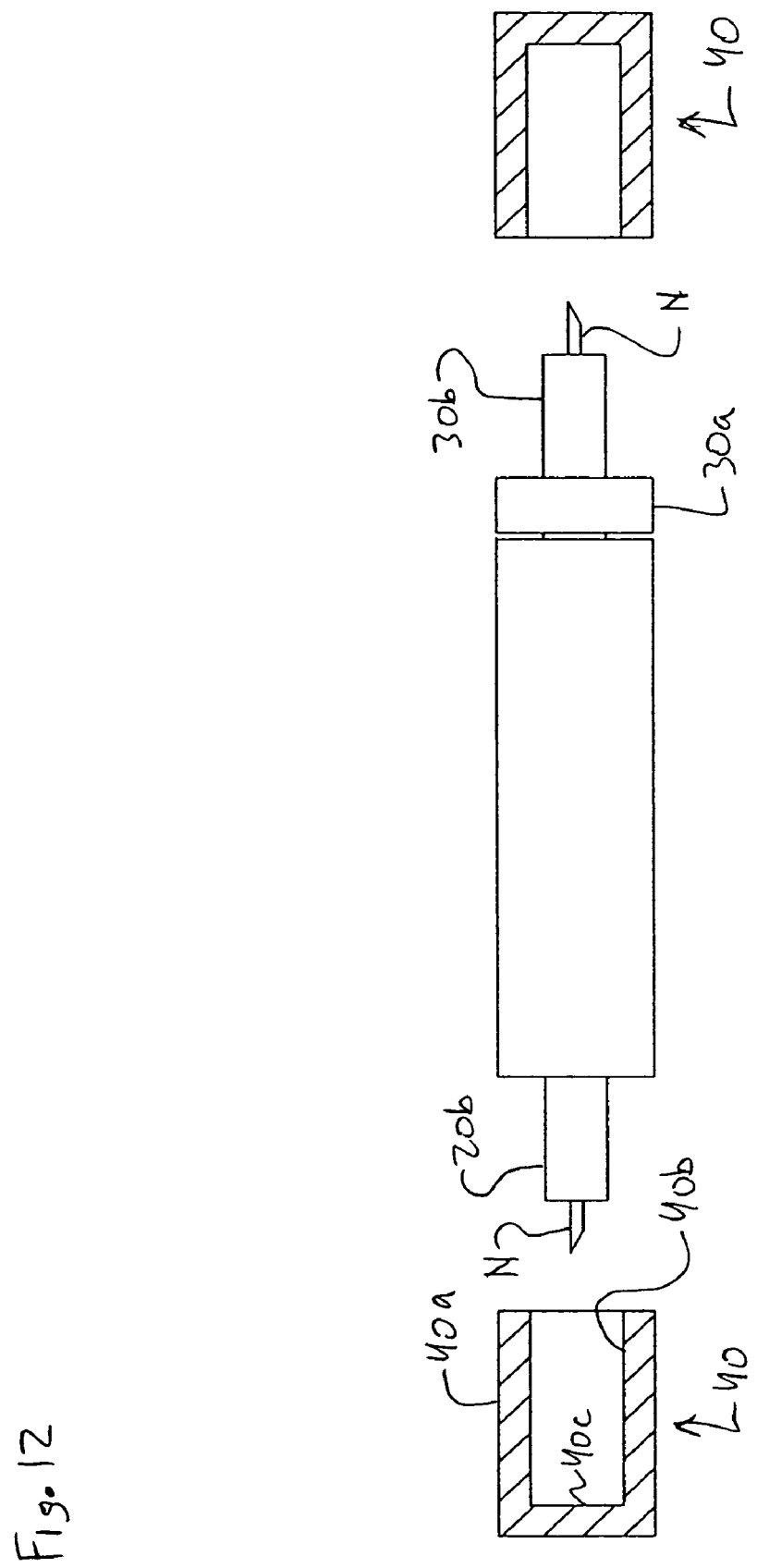
FIG. 12 shows another side view of the embodiment shown in FIG. 11 with the end caps disconnected and/or removed from the ends of the lancet body.

As can be seen in FIGS. 11 and 12, the caps 40 have an inner surface 40b which can be cylindrical which slides over and onto the projecting portions 20b, 30b of the end portions 20, 30. Although not shown in FIGS. 11-13,15 and 16, the invention contemplates some sort of mechanical connection between the caps 40 and the end portions 20, 30. In this regard, various non-limiting connection arrangements are shown in the drawings which can be used in this embodiment. Preferably, for the embodiment shown in FIGS. 11-13, 15 and 16, a connection arrangement of the type shown in FIGS. 17 and 18 is used in this embodiment. Most preferably, a connection system similar to that of FIGS. 32-35 is used in the embodiment of FIG. 11-13, 15 and 16. Each cap 40 also has a closed end 40c which is preferably spaced from the end of the needle N in order to prevent injury to the needle N.

Figure 13:
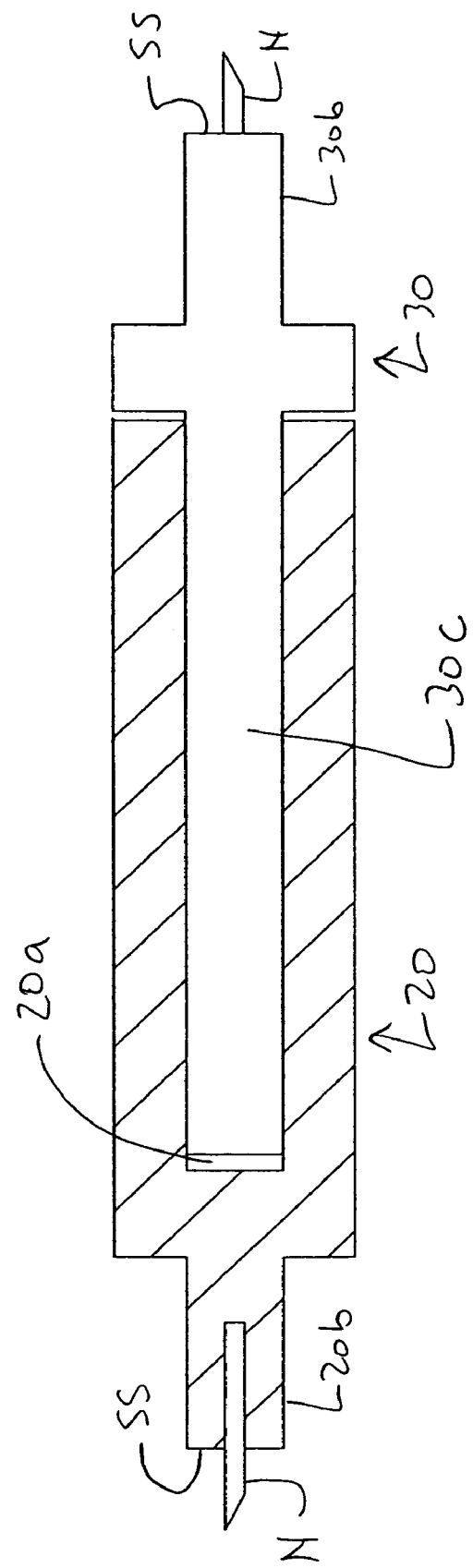
FIG. 13 shows another side view of the embodiment shown in FIG. 1 with the end caps removed. The left side or outer portion is shown in cross-section.

The second end portion 30 has a shoulder or flange portion 30a which can be of any size and shape and preferably correspond to a maim portion of the first portion 20. The right end 20c of the first end portion 20 is preferably arranged to abut (or to be slightly spaced therefrom) the flange 30a of the second end portion 30. As can be seen in FIGS. 13, 15 and 16, the first end portion 20 and the second end portion 30 are not identical in configuration as was the case in the previous embodiment. Instead, the second portion has been combined with the main portion in order to form a one-piece or integrally formed first portion 20. Portion 30 includes a flange portion 30a (as described above) as well as a front portion 30b which supports the needle N and whose front surface SS contacts the cap of the lancet device in order to define the penetration depth (see e.g., FIG. 31). Portion 30 further includes a rear portion 30c which is sized and shaped to connect with the inner opening 20a of the first portion 20. The length of generally cylindrical portion 30c and opening 20a can be any desired length and is preferably between 0.03 inches and 0.2 inches. Each portion 20 and 30 is preferably made as a one piece synthetic resin member that is formed with a metal needle N installed therein, e.g., in the same way that conventional lancets are formed. Preferably, the needle N projects from the stop surface SS by an amount that is typical of conventional lancets.

FIG. 14 shows a third non-limiting embodiment of a lancet assembly or double-ended lancet unit LA". This two-piece embodiment is similar to that of the previous embodiment shown in FIGS. 11-13, 15 and 16 except that a single lancet needle member is utilized having two projecting portions N. The unit LA" of this embodiment does not utilize a main body portion, and instead utilizes only a first end portion 200 and a second end portion 300. The first and second end portions 200, 300 are oriented in opposite directions. Each end portion 200, 300 also includes a cap (not shown but similar to caps 4, 40) to protect a lancet needle N, as will be described later on. The first portion 200 can have any desired cross-sectional shape such as polygonal, circular, or oval, and preferably is either triangular, square or circular in order to fit snugly into existing holding members of existing lancet devices. In the embodiment shown in FIG. 14, the first or outer portion 200 has a generally cylindrical shape having a length of between approximately 0.25 inches and approximately 1 inch and a diameter of between approximately 0.05 inches and approximately 0.3 inches. The particular size and shape of the lancet unit LA" can, of course, be adapted to the particular size and shape requirements of the lancet device as is the case with the previous embodiment. The first end portion 200 has an inner opening 200a which frictionally engages with an outer surface of portion 300c. Preferably, the opening 200a and the correspondingly shaped cylindrical portion 300c are sized and shaped so that the end portions 200 and 300 can be prevented from being removed or disconnected from each other once they are connected. This connection can be effectuated by any desired connection such as a press-fit connection, an adhesive connection, or an ultrasonic welding connection, etc,. As with the previous embodiment, the first and second portions 200 and 300 are preferably made of materials having different colors such as, e.g., blue and red and whose caps have substantially corresponding colors.

FIG. 17 shows one non-limiting way in which the cap C (which can be used on any of the embodiment disclosed herein) can be installed on either the front end portion FE or the second end portion SE (or both) of the lancet unit of the invention. In this embodiment, the cap C is substantially similar to that of the previous embodiments except that it includes a projecting portion PP which is frictionally received in a recess R formed on the first and/or second end portions FE, SE. Instead of a continuous ring-shaped projecting portion PP, the cap C can also use a plurality of partial projections (i.e., non-continuous or spaced apart) or even equally spaced circular projections to engage with the recess R. The projection PP preferably has a circular or outwardly curved end which is received in the correspondingly shaped recess R. This allows the cap C to removably connected to the first and/or second end portions FE, SE and to remain locked onto the lancet unit until removed by the user to expose the needle N. Removal of the cap C requires overcoming the frictional engagement of the projection PP and recess R and can be accomplished by pulling the cap C along a direction away from the lancet unit and generally parallel to an axis of the needle N.

FIG. 18 shows another non-limiting way in which the cap C' (which can be used on any of the embodiment disclosed herein) can be installed on either the front end portion FE' or the second end portion SE' (or both) of the lancet unit of the invention. In this embodiment, the cap C' is substantially similar to that of the previous embodiments except that it includes a projecting portion PP' formed ion the first and/or second end portions FE', SE' which frictionally engages with a recess R' formed in the cap C'. Instead of a continuous ring-shaped projecting portion PP', the first and/or second portions FE', SE' can also use a plurality of partial projections (i.e., non-continuous or spaced apart) or even equally spaced circular projections to engage with the recess R'. The projection PP' preferably has a circular or outwardly curved end which is received in the correspondingly shaped recess R'. This allows the cap C' to removably connected to the first and/or second end portions FE', SE' and to remain locked onto the lancet unit until removed by the user to expose the needle N. Removal of the cap C' requires overcoming the frictional engagement of the projection PP' and recess R' and can be accomplished by pulling the cap C' along a direction away from the lancet unit and generally parallel to an axis of the needle N.

FIGS. 19-24 show another non-limiting way in which the cap C" (which can be used on any of the embodiment disclosed herein) can be installed on either the front end portion FE" or the second end portion SE" (or both) of the lancet unit of the invention. In this embodiment, the cap C" is similar to that of the previous embodiments except that it is of a two-piece configuration (made up of rear part C1 and front part C2) which pieces are connected together via a wrapped connecting tape CT. The connecting tape CT provides a breakable connection allowing the front portion C2 of the cap C" to be separated from the rear portion C1 and removed to expose the needle N. The projecting portion or engaging member EM formed on the inner part C1 frictionally engages with an engaging recess ER formed in the cap C". The engaging portion EM is slofted (i.e., has at least two equally spaced slots SL) in order to allow the cap C" to be installed onto the recess ER. Instead of a continuous ring-shaped projecting portion EM, the portion or member EM can also be a plurality of partial projections (i.e., non-continuous or spaced apart) or even equally spaced circular projections to engage with the recess ER. The projection EM preferably has a tapered end and a shoulder which is non-removably received in the recess ER. This allows the rear portion C1 of the cap C" to be non-removably connected to the first and/or second end portions FE", SE" and to remain locked onto the lancet unit even after the front portion C2 is removed by the user (i.e., by breaking the tape CT) to expose the needle N. Removal of the front portion C2 of the cap C" requires overcoming the tension of and ripping of the wrapped connecting tape CT and can be accomplished by pulling the cap C" along a direction away from the lancet unit and generally parallel to an axis of the needle N (see FIGS. 23-24). The connecting tape CT, which overlaps substantially equal portions of the parts C1 and C2 and is attached thereto with, e.g., a pressure sensitive adhesive, can be of any desired material and is preferably of a material which tears with less than a few ounces of pulling force. Preferably, the tape CT is wrapped in a recess of the cap C" so that it cannot be inadvertently removed.

Figure 25:
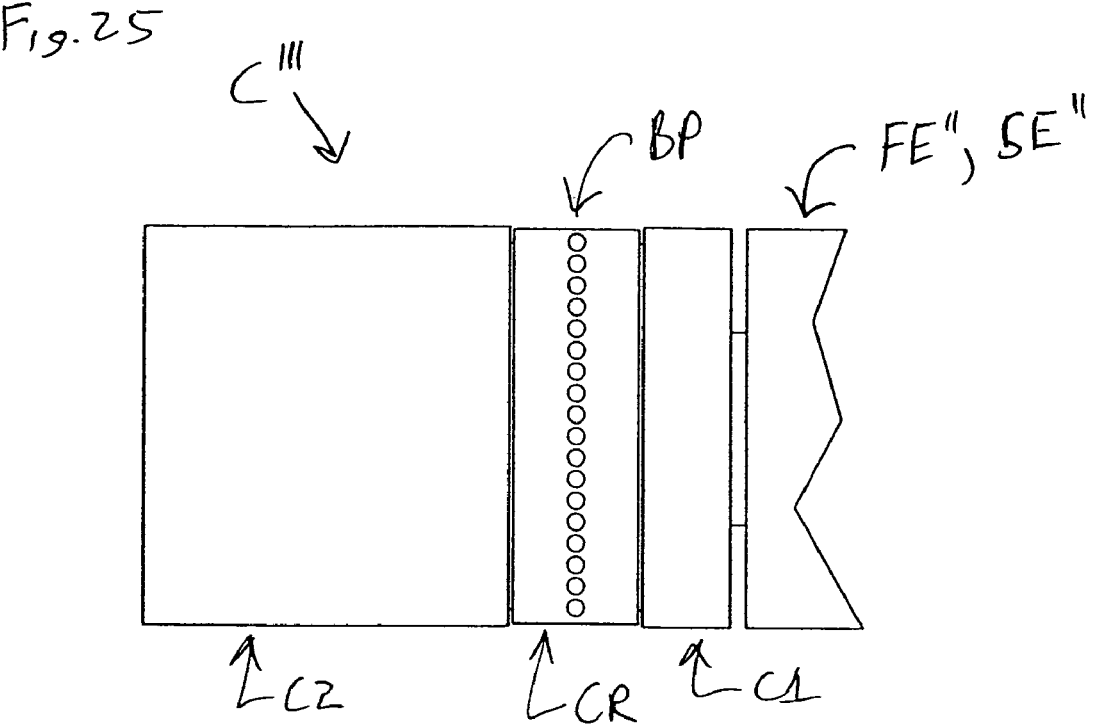
FIG. 25 shows a partial side view of still another way that the caps of any of the embodiments disclosed herein can be secured to the lancet body. In this embodiment, the cap is of a three-piece construction in which two main pieces are connected together via a breakable sleeve piece arranged about the connection between the two main pieces.
Figure 26:
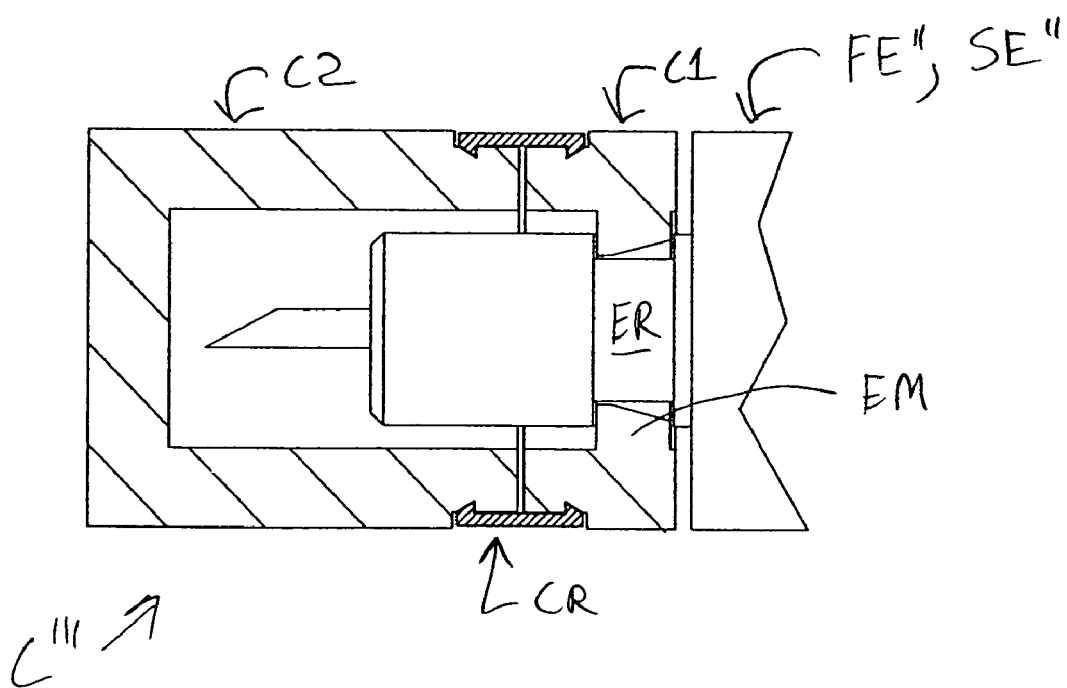
FIG. 26 shows a side cross-section view of FIG. 25.

FIGS. 25 and 26 show another non-limiting way in which the cap $C^{111}$ (which can be used on any of the embodiment disclosed herein) can be installed on either the front end portion FE" or the second end portion SE" (or both) of the lancet unit of the invention. In this embodiment, the cap $C^{111}$ is similar to that of the previous embodiments except that it is of a two-piece configuration (made up of rear part C1 and front part C2) which pieces are connected together via a connecting ring CR. The connecting ring CR provides a breakable connection along the breakable perforations BP allowing the front portion C2 of the cap $C^{111}$ to be separated from the rear portion C1 and removed to expose the needle N. The projecting portion or engaging member EM formed on the inner part C1 frictionally engages with an engaging recess ER formed in the cap $C^{111}$. The engaging portion EM is slotted (i.e., has at least two equally spaced slots SL as in the previously described embodiment) in order to allow the cap $C^{111}$ to be installed onto the recess ER. Instead of a continuous ring-shaped projecting portion EM, the portion or member EM can also be a plurality of partial projections (i.e., non-continuous or spaced apart) or even equally spaced circular projections to engage with the recess ER. The projection EM preferably has a tapered end and a shoulder which is non-removably received in the recess ER. This allows the rear portion C1 of the cap $C^{111}$ to be non-removably connected to the first and/or second end portions FE", SE" and to remain locked onto the lancet unit even after the front portion C2 is removed by the user (i.e., by breaking the connecting ring CR) to expose the needle N. Removal of the front portion C2 of the cap $C^{111}$ requires overcoming the tension of and ripping of the connecting ring CR along the perforations BP and can be accomplished by pulling the cap $C^{111}$ along a direction away from the lancet unit and generally parallel to an axis of the needle N (in the same was as FIGS. 23-24). The connecting ring CR, which overlaps substantially equal portions of the parts C1 and C2 and is attached thereto with, e.g., a end projections that engage with correspondingly shaped recesses, can be of any desired material and is preferably of a material which tears or breaks along the perforations BP with less than a few ounces of pulling force. Preferably, the ring CR is arranged in a recess of the cap $C^{111}$ so that it cannot be inadvertently removed.

Figure 27:
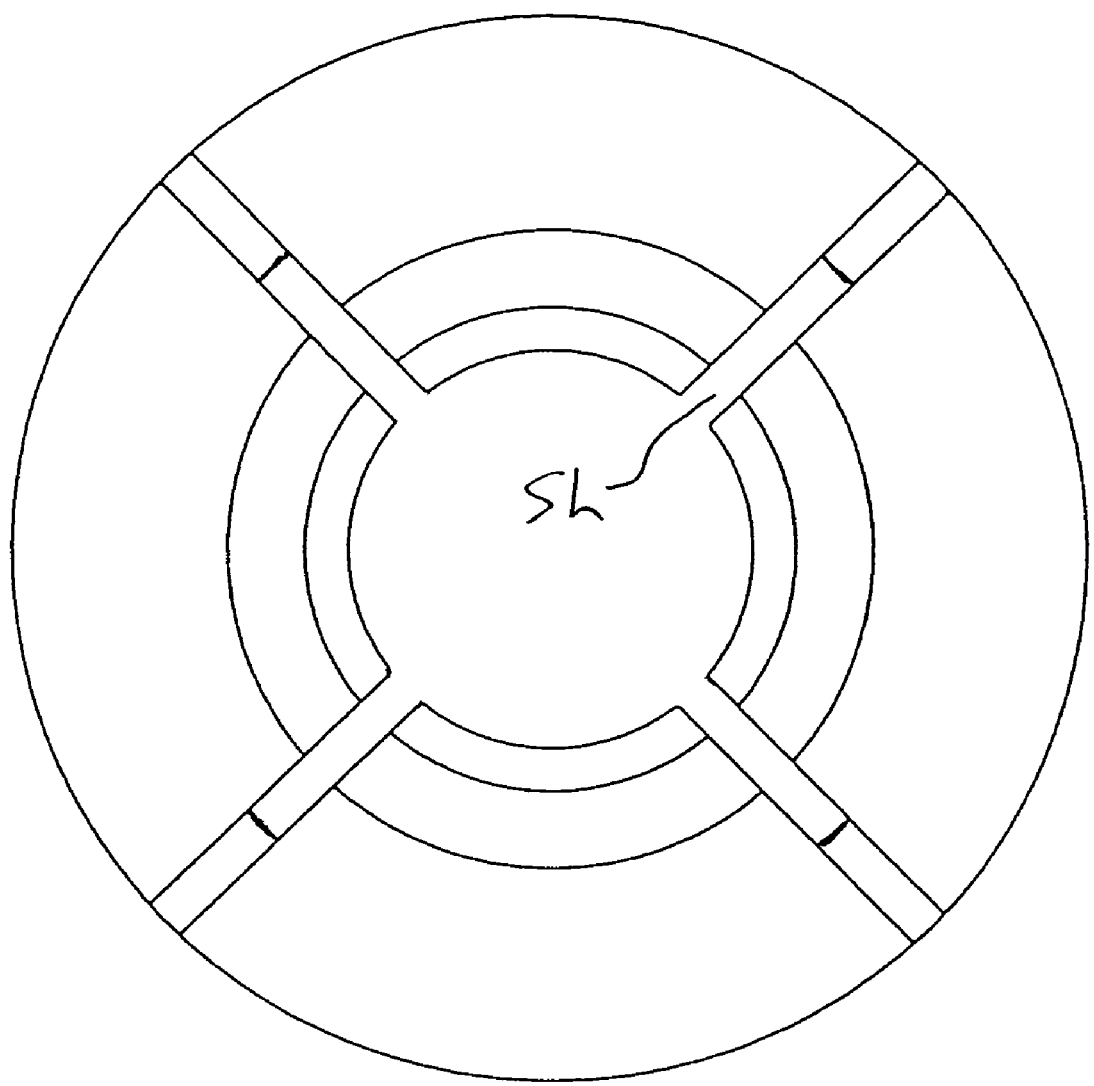
FIG. 27 shows an enlarged end view of the caps shown FIGS. 22 and/or 26.

FIG. 27 illustrates one non-limiting slot configuration for the caps shown in FIGS. 19-26. This exemplary configuration uses four equally spaced slots SL. However, the invention contemplates using as few as one and as many as e.g., 12. Since the purpose of the slots SL is to ensure easy installation of the caps onto the lancet unit, one should provide as many slots SL as is needed for this purpose.

Figure 28:
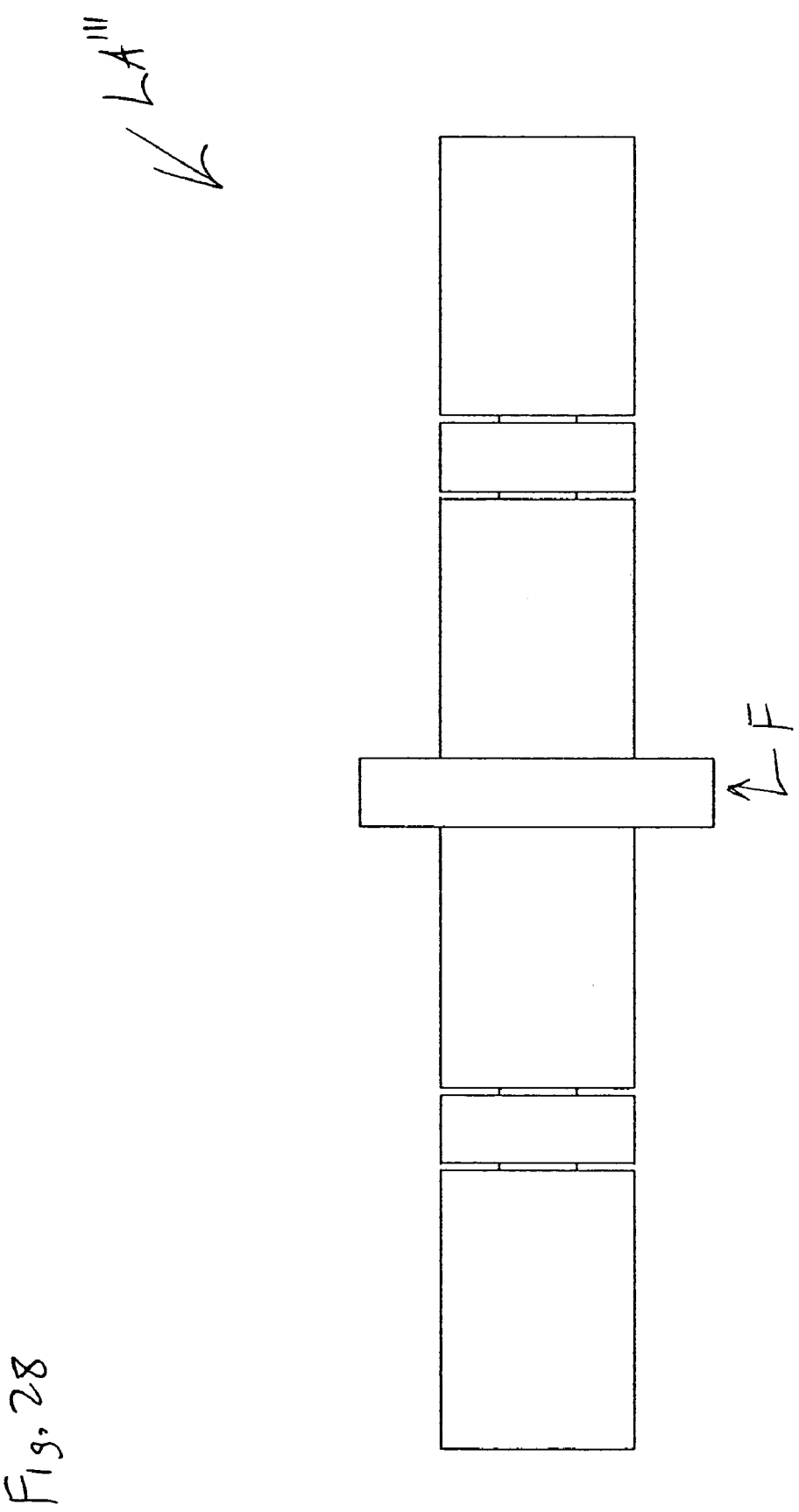
FIG. 28 shows another embodiment of the lancet unit of the invention. This embodiment is similar to that of FIG. 1 except that it additionally includes a centrally disposed projecting flange.

FIG. 28 shows another embodiment of the lancet unit $LA^{111}$ of the invention. This embodiment is similar to that of FIGS. 1-10 except that it additionally includes a generally centrally disposed projecting flange F. The flange F is preferably sized and shaped in a manner which allows the lancet unit to be properly installed/mounted to the holding member of the lancet device.

Figure 29:
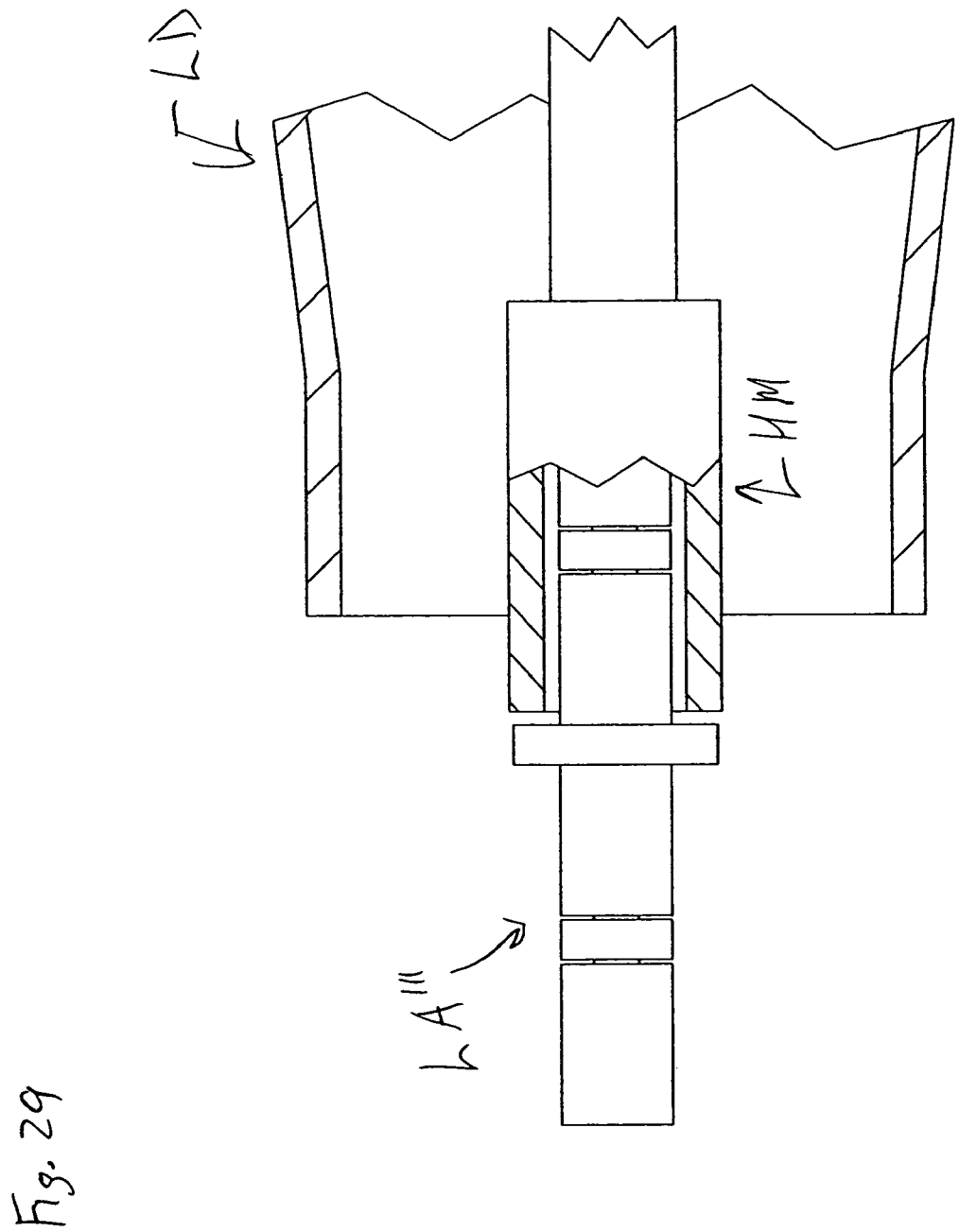
FIG. 29 shows an enlarged partial view of a lancet device having a lancet holding member which can support or retain the lancet unit disclosed herein. This Figure shows the lancet unit of FIG. 28 installed on the holding member.
Figure 30:
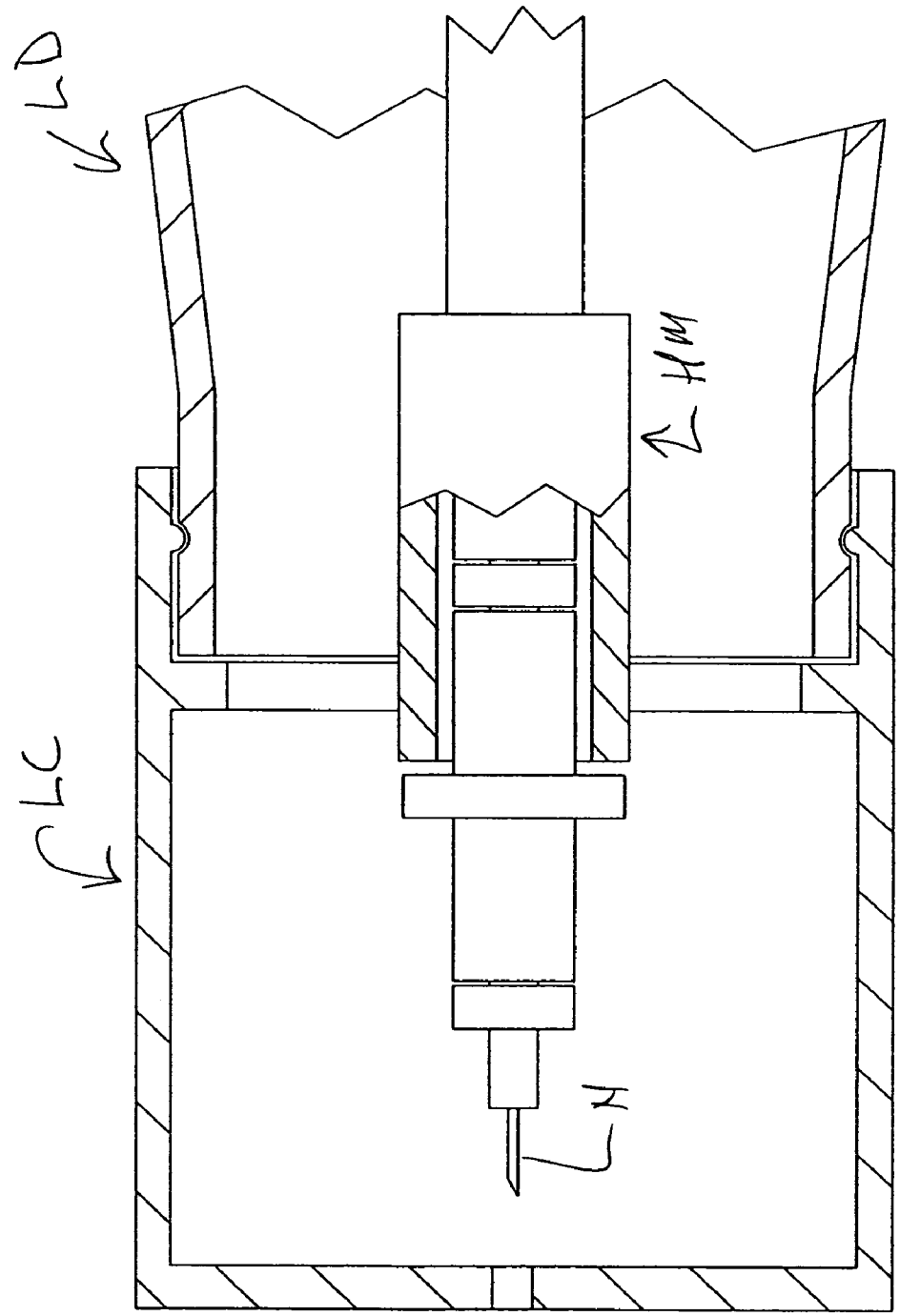
FIG. 30 shows an enlarged partial view of FIG. 29 with the lancet device cap installed on the front end of the lancet device.
Figure 31:
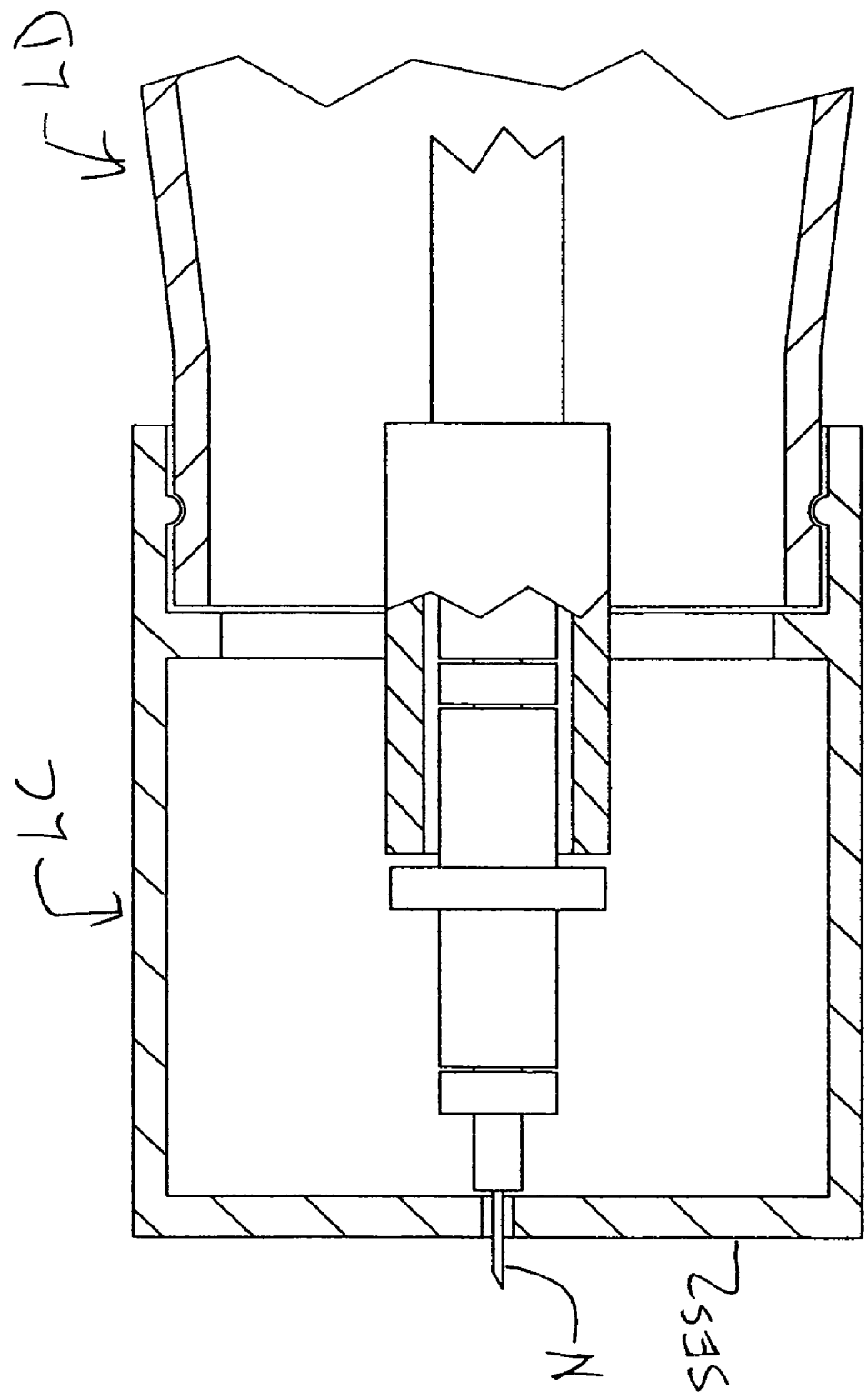
FIG. 31 shows an enlarged partial view of FIG. 30 after the lancet and holding member have moved to the fully extended position.
Figure 32:
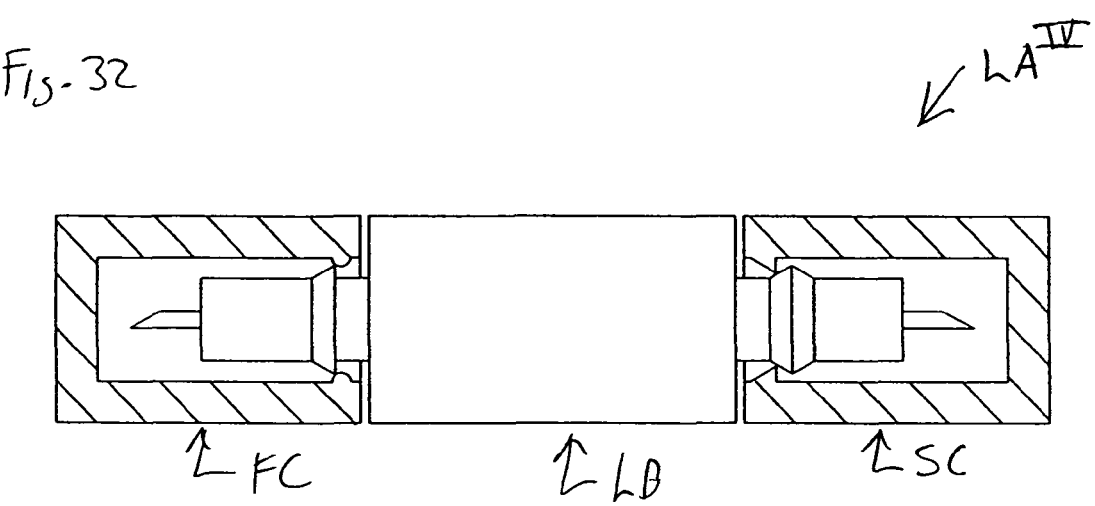
FIG. 32 shows still another embodiment of the lancet unit of the invention. This embodiment is similar to that of FIG. 1 except that it uses different connections between the left side cap and the left end of the lancet body and between the right side cap and the right end of the lancet body. As a result of this arrangement, the right side cap can be removed from the right end and installed onto the left end of the lancet body and is thereafter prevented from be removed therefrom.

FIG. 29 shows, by way of non-limiting example, an enlarged partial view of a lancet device LD having a lancet holding member HM which can support or retain the lancet unit $LA^{111}$. Of course, the lancet device LD can also be fitted with any of the lancet units disclosed and/or claimed herein. This Figure shows the lancet unit of FIG. 28 installed on the holding member HM only by way of example. FIG. 30 shows an enlarged partial view of FIG. 29 with the lancet device cap LC installed on the front end of the lancet device LD. The lancet cap LC is installed after the cap is removed from the lancet unit $LA^{111}$ to expose the needle N. FIG. 31 shows an enlarged partial view of FIG. 30 after the lancet needle N projects past the skin engaging surface SES and after the holding member HM has moved to the fully extended position.

Figure 33:
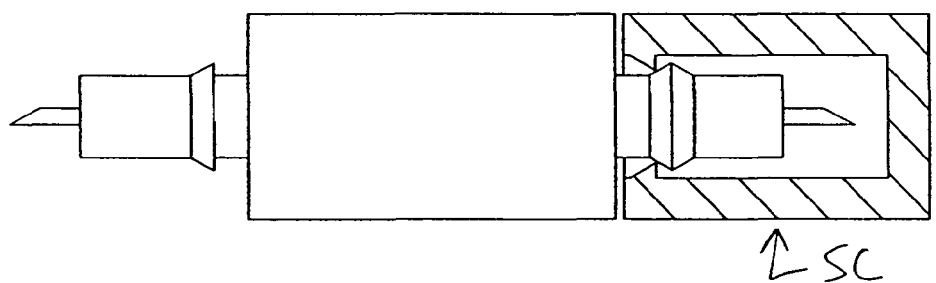
FIG. 33 shows the embodiment of FIG. 32 with the left side cap removed from the left end.
Figure 34:
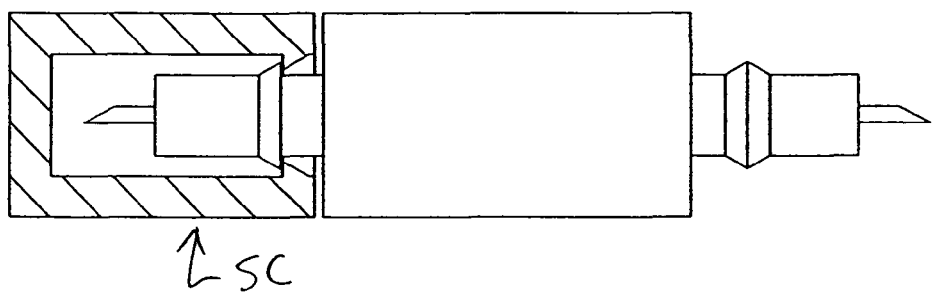
FIG. 34 shows the embodiment of FIG. 32 with the right side cap removed from the right end and installed on the left end in a manner which prevents its removal therefrom.
Figure 35:
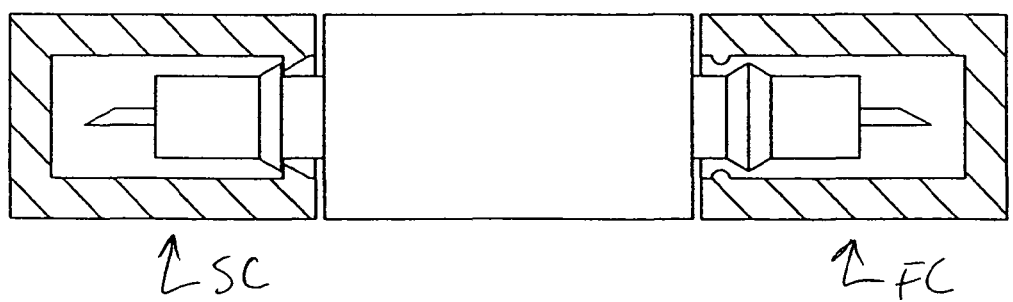
FIG. 35 shows the embodiment of FIG. 32 with the right side cap non-removably installed on the left end and with the left side cap removably installed on the right end.
Figure 40:
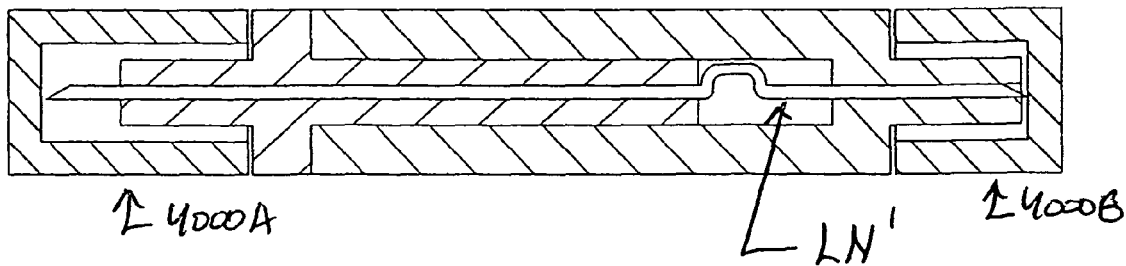
FIG. 40 shows still another embodiment of the lancet unit of the invention. This embodiment is similar to that of FIGS. 36-39 except that it uses different configuration lancet needle. In the position shown in FIG. 40, the right side cap moves the right side pointed end of the needle so as to be substantially flush with the right axial end face of the outer part of the body. The right side cap also prevents the lancet needle from moving axially to the right.
Figure 41:
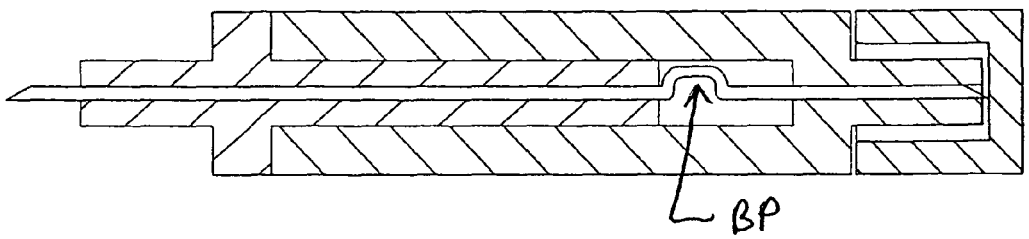
FIG. 41 shows the embodiment of FIG. 40 with the left side cap removed from the left end.
Figure 42:
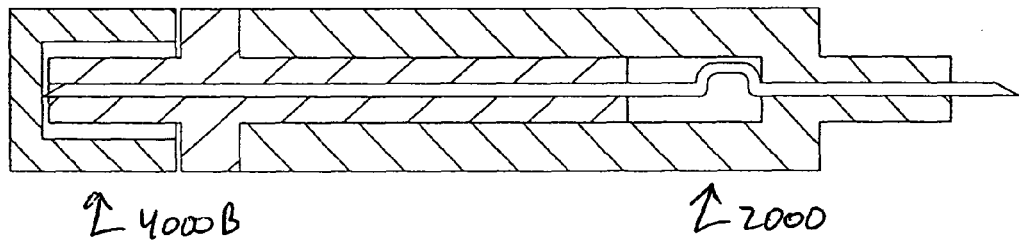
FIG. 42 shows the embodiment of FIG. 40 with the right side cap removed from the right end and installed on the left end. Installation of the right cap on the left end causes the lancet needle to move axially to the right.
Figure 43:
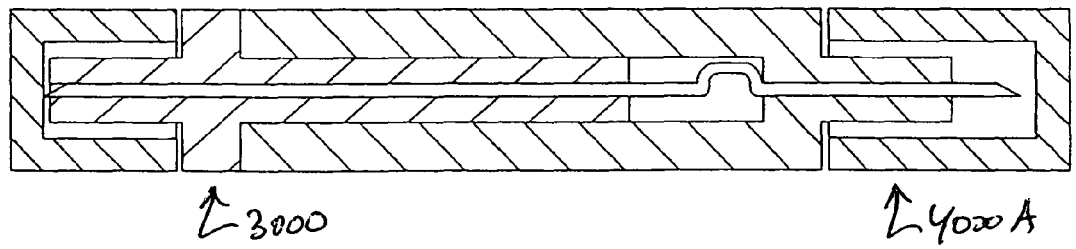
FIG. 43 shows the embodiment of FIG. 40 with the right side cap installed on the left end and with the left side cap installed on the right end.

FIGS. 32-35 show still another embodiment of the lancet unit $LA^{IV}$ of the invention. This embodiment is similar to that of FIG. 1 except that it uses different connections between the first or left side cap FC and the left end of the lancet body LB and between the second or right side cap SC and the right end of the lancet body LB. As a result of this arrangement, the right side cap SC can be removed from the right end and installed onto the left end of the lancet body LB and is thereafter prevented from be removed therefrom. FIG. 33 shows the embodiment of FIG. 32 with the left side cap FC removed from the left end. This allows the left side lancet needle to be used in a lancet device. FIG. 34 shows the embodiment of FIG. 32 with the right side cap SC removed from the right end and installed on the left end in a manner which prevents its removal therefrom. FIG. 35 shows the embodiment of FIG. 32 with the right side cap FC non-removably installed on the left end and with the left side cap FC removably installed on the right end.

The benefits of such an arrangement is as follows: a user installs the lancet unit $LA^{IV}$ onto a holding member of the lancet device (in a similar manner to that shown in FIG. 29) with, e.g., the blue first cap FC projecting out from the holding member. Then, he or she removes the blue cap FC and uses the lancet device to prick the skin. Then, instead of discarding the lancet unit $LA^{IV}$ (as is the case with the prior art lancets), he or she removes the lancet unit $LA^{IV}$ from the holding member and removes the red cap SC from the blue body LB, installs the red cap SC on the end which previously has the blue cap FC. Then, he or she re-installs the lancet unit $LA^{IV}$ into the holding member with the right end projecting from the holding member. The user is now free to prick the skin with another clean needle. After use, the user will know that the lancet unit $LA^{IV}$ is used up because, once removed from the holding member, the user will see that red cap SC is installed on the blue left end-indicating that that needle has been used already. He or she can then install the blue cap FC on the right end (see FIG. 35) and discard the lancet unit $LA^{IV}$. This process doubles the useful file of the lancet.

By way of non-limiting examples, the lancet unit can be used with a lancet device (i.e., any of the lancet devices disclosed herein) which includes an adjustable tip or front cap of the type described in any one of the following documents: U.S. Pat. No. 6,811,557 to SCHRAGA, U.S. Pat. No. 6,530, 937 to SCHRAGA, U.S. Pat. No. 6,322,575 to SCHRAGA, and U.S. Pat. No. 5,613,978 to HARDING, the disclosures of which are hereby expressly incorporated by reference in their entireties. By way of non-limiting examples, the lancet unit can also be used with a lancet device (i.e., any of the lancet devices disclosed herein) which includes a non-adjustable tip or front cap (see FIG. 30) of the type described in any one of the following documents: U.S. Pat. No. 6,156,051 to SCHRAGA, U.S. Pat. No. 6,022,366 to SCHRAGA, U.S. Pat. No. 5,908,434 to SCHRAGA, U.S. Pat. No. 5,797,942 to SCHRAGA, U.S. Pat. No. 5,628,764 to SCHRAGA, and U.S.

Pat. No. 5,464,418 to SCHRAGA, the disclosures of which are hereby expressly incorporated by reference in their entireties. The above noted tips, as well as any of the tips known in the prior art, can also be used with any of the lancet devices described herein such as the ones shown in FIGS. 29-31. Additionally, the tip or front cap can be secured (e.g., non-removably secured or removably secured) to the lancet devices disclosed herein by any conventionally known arrangements such as threads, a snap connection (see FIGS. 30-31), etc,.

The portions other than the needles of the lancet units can be made of any conventional material of which conventional lancets are made such as, e.g., synthetic resin. They can also be made by any conventional lancet making techniques including, e.g., injection molding, extrusion, etc,. The lancet needles can also be of the same material, types and sizes as are used in conventional lancets. By way of non-limiting example, each lancet unit can also range in axial length between approximately ¼" and approximately ¾".

FIGS. 29-31 illustrate one non-limiting way in which the unit can be mounted to a lancet holding member of a lancet device. Generally speaking, most lancet devices utilize a lancet holding member. The lancet holding member is typically movably mounted within the lancet device and is usually moved and/or biased by one or more springs. In many lancet devices, the lancet holding member retains a replaceable lancet at a front location. Examples of such devices are disclosed in the following documents: U.S. Pat. No. 6,811,557 to SCHRAGA, U.S. Pat. No. 6,530,937 to SCHRAGA, U.S. Pat. No. 6,346,114 to SCHRAGA, U.S. 6,190,398 to SCHRAGA, U.S. Pat. No. 6,156,051 to SCHRAGA, U.S. Pat. No. 6,022,366 to SCHRAGA, U.S. Pat. No. 5,908,434 to SCHRAGA, U.S. Pat. No. 5,797,942 to SCHRAGA, U.S. Pat. No. 5,628,764 to SCHRAGA, U.S. Pat. No. 5,464,418 to SCHRAGA, and U.S. Pat. No. 5,613,978 to HARDING, the disclosures of which are hereby expressly incorporated by reference in their entireties. According to one non-limiting example, the lancet holding member of one or more of the devices disclosed in these documents is modified so as to use the unit disclosed herein. This can occur by redesigning the lancet holding member of these devices so as to be hollow or tubular to allow for axial insertion of the unit in a manner similar to that shown in the lancet device of, e.g., FIGS. 29-31.

FIGS. 36-39 show another non-limiting embodiment of the double-ended lancet. The lancet unit has a two-piece body 1000 made up of body parts 2000 and 3000 (similar to those of FIG. 14), and two end caps 4000A and 4000B. The caps 4000A and 4000B can be attached to the body 1000 using any of the mechanisms disclosed herein. A freely movable lancet needle LN is able to slide axially back and forth between the positions shown in FIGS. 37 and 38. The movement of the lancet needle LN is limited between these axial positions by a movable stop MS (which can be molded synthetic resin cylindrical member) that is axially fixed to the lancet needle LN. In this embodiment, two different size caps 4000A and 4000B are utilized. The benefits of such an arrangement is as follows: a user installs the lancet unit shown in FIG. 36 onto a holding member of the lancet device (in a similar manner to that shown in FIG. 29) with, e.g., the first cap 4000A projecting out from the holding member. Then, he or she removes the cap 4000A (see FIG. 37) and uses the lancet device to prick the skin. Then, instead of discarding the lancet unit (as is the case with the prior art lancets), he or she removes the lancet unit from the holding member and removes the second cap 4000B from the body 1000, installs the second cap 4000B on the end which previously has the first cap 4000A (see FIG. 38). Because the lancet needle LN is freely movably mounted in body parts 2000 and 3000, installing the cap 4000B on the left end causes the lancet needle LN to move to the position shown in FIG. 38. Then, he or she re-installs the lancet unit into the holding member with the right end projecting from the holding member. The user is now free to prick the skin with another clean needle. After use, the user will know that the lancet unit is expended because, once removed from the holding member, the user will see that second cap 4000B is installed on the left end—indicating that that needle has been used already. This indication will clear because the first cap 4000A is made to have the substantially same color as part 3000 (e.g., red) and the second cap 4000B is made to have substantially the same color as the other part 2000 (e.g., blue). He or she can then install the red cap 4000A on the blue end (see FIG. 39) and discard the lancet unit. Thus, when fully used, the red cap 4000A will be installed on the blue part 2000 and the blue cap 4000B will be installed on the red part 3000. This process doubles the useful file of the lancet.

FIGS. 40-43 show another non-limiting embodiment of the double-ended lancet. The lancet unit is substantially similar to the embodiment shown in FIGS. 36-39 except that the freely movable lancet needle LN'has a bent portion BP instead of a molded movable stop. The bent portion BP functions to limit the axial movement of the lancet needle LN'between the axial positions shown in FIGS. 41.

Figure 44:
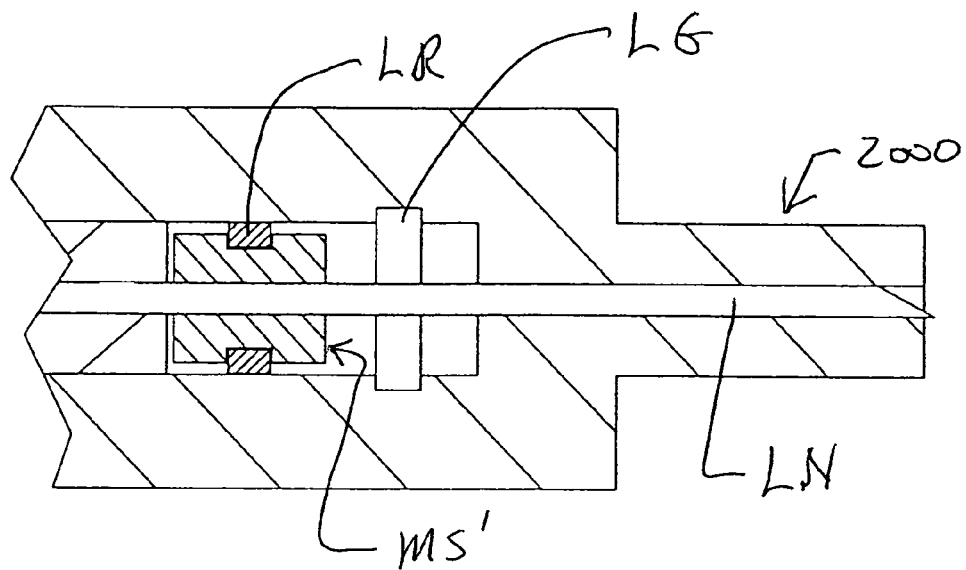
FIG. 44 shows an enlarged partial view of another embodiment similar to that of FIGS. 36-39 except that it additionally includes an arrangement for locking the lancet needle in an axial position.
Figure 45:
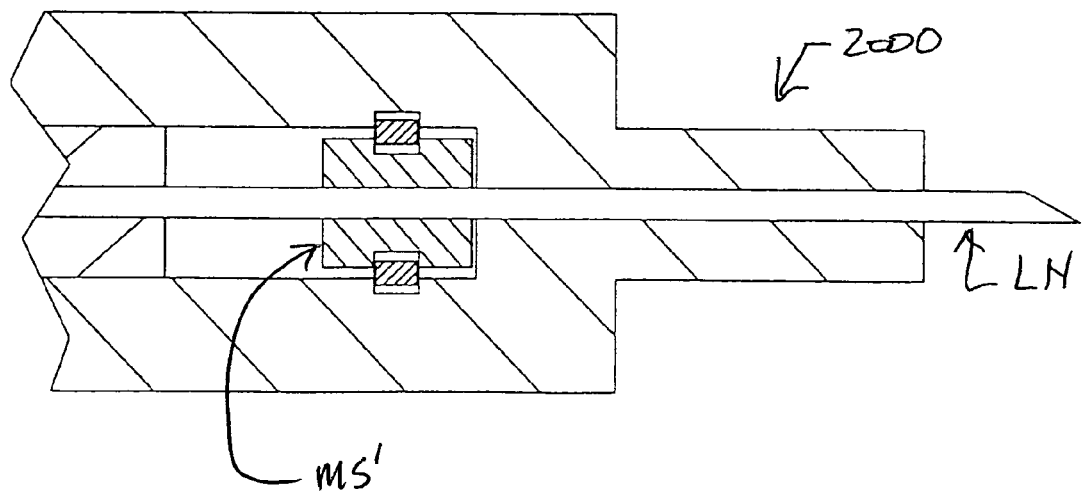
FIG. 45 shows the embodiment of FIG. 44 after the lancet needle has been moved axially and has been locked in an axial position.

FIGS. 44 and 45 show another non-limiting embodiment of the double-ended lancet. The lancet unit is substantially similar to the embodiment shown in FIGS. 36-39 except that the movable stop MS'is lockable in the positions shown in FIGS. 38 and 39. The locking occurs between a snap or lock ring LR arranged on the movable stop MS' and a locking groove LG formed in the body part 2000. A similar locking arrangement may also be provided on the embodiment shown in FIGS. 40-43.

The lancet devices can preferably made transparent and/or translucent so that a user will clearly be able to see the inner workings of the device and note how much of the unit has already been utilized. Of course, the invention is not limited to a body design which is transparent and/or translucent.

All the parts of the lancet device, with the exception of the springs and needles (which can respectively be made of spring steel and stainless steel), may be made from plastic materials and can be formed using conventional injection molding techniques or other known manufacturing methods. However, when practical, other materials and manufacturing processes may also be utilized. In each of the disclosed embodiments, the lancets which make up the multi-lancet unit can be formed individually (e.g., by injection molding) and then connected together as described above. However, the invention also contemplates forming the multi-part lancet unit (e.g., by injection molding) as a one-piece member. In this latter case, the lancet needles can be placed (e.g., at predetermined locations) within the mold(s) which will form the multi-lancet unit. Then, the mold(s) is filled with the melted plastic material. Of course, provision is made in the mold(s) for producing the breakable connections will allow the lancets to be separated from the unit.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A double-ended lancet unit for a lancet device, the unit comprising:
   a lancet body having a first end and a second end and being sized and configured to frictionally engage with a holding member of the lancet device;
   at least one of:
      a first lancet needle projecting from the first end and a second lancet needle projecting from the second end; and
      a lancet needle member having oppositely arranged pointed ends and being movably mounted to the lancet body;
   the lancet body being made of a material different from that of the first and second needles or the pointed ends;
   first and second removable caps respectively removably connected to the first and second ends; and
   at least one of the first and second removable caps being re-installable on one of the first and second ends of the double-ended lancet unit,
   wherein the double-ended lancet unit is installable on the lancet device and each of the first and second lancet needles or the pointed ends is structured and arranged to prick a user's skin to obtain a blood sample and is not usable for fluid injection.

2. The unit of claim 1, wherein the lancet body comprises a one-piece integrally formed member.

3. The unit of claim 1, wherein the lancet body comprises a one-piece synthetic resin member.

4. The unit of claim 1, wherein the lancet body comprises a two-piece member with non-removably connected portions.

5. The unit of claim 1, wherein the lancet body comprises a two-piece member with removably connected portions.

6. The unit of claim 1, wherein the first and second lancet needles are made of metal and project from the first and second ends by substantially a same amount.

7. The unit of claim 1, wherein the lancet unit has an overall length which between approximately 0.25 inches and approximately 1.50 inches.

8. The unit of claim 1, wherein the lancet body is generally cylindrical.

9. The unit of claim 1, wherein the lancet body comprises a diameter that is between approximately 0.125 inches and approximately 0.375 inches.

10. The unit of claim 1, wherein the body is generally cylindrical.

11. The unit of claim 1, wherein the first and second caps respectively have portions that are non-removably connected to the first and second ends.

12. The unit of claim 1, wherein the first cap is removably connected to the first end, and once installed on the second end, is non-removably connected to the second end.

13. The unit of claim 12, wherein the second cap removably connected to the second end, and being capable of being installed on the first end.

14. The unit of claim 12, wherein the second cap removably connected to the second end, and once installed on the first end, is non-removably connected to the first end.

15. The unit of claim 1, wherein the lancet body comprises a main portion and first and second portions connected to the main portion.

16. The unit of claim 1, wherein the lancet body comprises an outer member and an inner member extending at least partially into the outer member.

17. The unit of claim 1, wherein the lancet body comprises one of a polygonal cross-section, an oval cross-section, a non-circular cross-section, and a circular cross-section.

18. The unit of claim 1, wherein the first and second caps are respectively connected to the first and second ends via respective first and second locking mechanisms.

19. The unit of claim 1, wherein the first and second caps are respectively connected to the first and second ends via respective first and second breakable connection mechanisms.

20. A lancet device utilizing the double-ended lancet unit of claim 1, the lancet device comprising:
   a body; and
   a holding member which removably retains the double-ended lancet unit.

21. A lancet device utilizing the double-ended lancet unit of claim 1, the lancet device comprising:
   a body;
   a trigger; and
   a movable holding member which removable retains the double-ended lancet unit.

22. A lancet device utilizing the double-ended lancet unit of claim 1, the lancet device comprising:
   a body;
   a trigger;
   a movable holding member which retains the double-ended lancet unit; and
   a mechanism for moving the holding member to a retracted trigger-set position.

23. A lancet device utilizing the double-ended lancet unit of claim 1, the lancet device comprising:
   a body;
   a holding member which retains the double-ended lancet unit; and
   a cap removably connected to the body.

24. A method of puncturing a surface of skin using the lancet device of claim 23, the method comprising:
   arranging the lancet device adjacent against a user's skin; and
   triggering the lancet device so that one of the first and second lancet needles is caused to penetrate the user's skin.

25. A method of puncturing a surface of skin using the lancet device of claim 23, the method comprising:
   arranging the cap adjacent against a user's skin;
   triggering the lancet device so that the first lancet needle is caused to penetrate the user's skin;
   removing the lancet unit from the holding member and re-installing the lancet unit onto the holding member; and
   again triggering the lancet device so that the second lancet needle is caused to penetrate the user's skin.

26. The method of claim 25, further comprising: disconnecting, before the removing, the first cap from the first end and installing the first cap on the second end.

27. A method of puncturing a surface of skin using the lancet device of claim 20, the method comprising:
   installing the lancet unit onto the holding member;
   disconnecting the first cap from the first end;
   arranging the lancet device adjacent against a user's skin;

triggering the lancet device so that the first lancet needle is caused to penetrate the user's skin;
removing the lancet unit from the holding member;
disconnecting the second cap from the second end and installing the second cap on the first end;
re-installing the lancet unit onto the holding member; and
again triggering the lancet device so that the second lancet needle is caused to penetrate the user's skin.

28. A double-ended lancet unit for a lancet device, the unit comprising:
   a body having first and second generally symmetrically-shaped ends and being sized and configured to frictionally engage with a holding member of the lancet device;
   a first lancet needle projecting from a center of a generally planar surface arranged on the first end;
   a second lancet needle projecting from a center of a generally planar surface arranged on the second end;
   a first cap removably connected to the first end;
   a second cap removably connected to the second end;
   the body being made of a material different from that of the first and second needles; and
   at least one of the first and second removable caps being re-installable on one of the first and second ends of the double-ended lancet unit,
   wherein the double-ended lancet unit is installable on the lancet device and is not usable for fluid injection.

29. The unit of claim 28, wherein the body comprises a color X.

30. The unit of claim 29, wherein the first cap comprises a color substantially similar to color X.

31. The unit of claim 30, wherein the second cap comprises a color that is substantially different from color X.

32. The unit of claim 28, wherein the body and the first cap have substantially the same color and the second cap comprises a different color than the body.

33. A double-ended lancet unit for a lancet device, the unit comprising:
   a body having first and second generally symmetrical ends and being sized and configured to frictionally engage with a holding member of the lancet device;
   a first lancet needle projecting from a center of a generally planar surface arranged on the first end;
   a second lancet needle projecting from a center of a generally planar surface arranged on the second end;
   a first cap connected to the first end via one of a breakable connection and a locking connection;
   a second cap connected to the second end via one of a breakable connection and a locking connection;
   the body being made of a material different from that of the first and second needles; and
   at least one of the first and second removable caps being re-installable on one of the first and second ends of the double-ended lancet unit,
   wherein the double-ended lancet unit is installable on the lancet device and is not usable for fluid injection.

34. The unit of claim 33, wherein the body and the first cap have substantially the same color and the second cap comprises a different color than the first cap and the body.

35. The unit of claim 33, wherein, once removed from the first end and installed on the second end, the first cap remains non-removably connected to the second end.

* * * * *